(12) United States Patent
Reisenburg Molson et al.

(10) Patent No.: US 10,737,030 B2
(45) Date of Patent: Aug. 11, 2020

(54) FLUID DELIVERY DEVICE AND METHOD

(71) Applicant: Iinjec Technologies, Inc., Quebec (CA)

(72) Inventors: Catherine Reisenburg Molson, Quebec (CA); Alexandra Molson, Quebec (CA); Jake Ganem, Cape Neddick, ME (US)

(73) Assignee: IINJEC TECHNOLOGIES INC., Montreal, Quebec (CA)

( * ) Notice: Subject to any disclaimer, the term of this patent is extended or adjusted under 35 U.S.C. 154(b) by 687 days.

(21) Appl. No.: 14/441,613

(22) PCT Filed: Nov. 11, 2013

(86) PCT No.: PCT/IB2013/003057
§ 371 (c)(1),
(2) Date: May 8, 2015

(87) PCT Pub. No.: WO2014/096957
PCT Pub. Date: Jun. 26, 2014

(65) Prior Publication Data
US 2016/0008544 A1 Jan. 14, 2016

Related U.S. Application Data

(60) Provisional application No. 61/830,895, filed on Jun. 4, 2013.

(51) Int. Cl.
*A61M 5/28* (2006.01)
*A61M 5/315* (2006.01)
(Continued)

(52) U.S. Cl.
CPC .......... *A61M 5/282* (2013.01); *A61M 5/2033* (2013.01); *A61M 5/283* (2013.01);
(Continued)

(58) Field of Classification Search
CPC .............. A61M 5/3294; A61M 5/3234; A61M 5/2033; A61M 5/322; A61M 5/3221;
(Continued)

(56) References Cited

U.S. PATENT DOCUMENTS

| | | | |
|---|---|---|---|
| 2,769,443 | A | 9/1954 | Dunmire |
| 2,704,072 | A | 3/1955 | Sarnoff |

(Continued)

FOREIGN PATENT DOCUMENTS

| | | |
|---|---|---|
| CN | 1702271 A | 1/2006 |
| CN | 101522235 A | 9/2009 |

(Continued)

OTHER PUBLICATIONS

International search report No. PCT/IB2013/003057.
(Continued)

*Primary Examiner* — Nathan R Price
*Assistant Examiner* — Anh Bui

(57) ABSTRACT

A fluid delivery injector comprises a syringe defining a barrel; a plunger and a hollow needle provided within the barrel adapted for linear movement parallel to a longitudinal axis with a distal tip of the needle contained within the syringe. A fluid retention reservoir is defined at least in the barrel and is in fluid communication with the needle when pressure is applied to the fluid in the reservoir and to the plunger for moving the needle out of the barrel. A spring may be provided for retracting the needle when pressure is released from the plunger.

19 Claims, 18 Drawing Sheets

(51) Int. Cl.
*A61M 5/32* (2006.01)
*A61M 5/20* (2006.01)

(52) U.S. Cl.
CPC .......... *A61M 5/284* (2013.01); *A61M 5/288* (2013.01); *A61M 5/3157* (2013.01); *A61M 5/322* (2013.01); *A61M 5/3221* (2013.01); *A61M 5/3232* (2013.01); *A61M 5/3287* (2013.01); *A61M 5/3294* (2013.01); *A61M 5/3298* (2013.01); *A61M 5/3234* (2013.01); *A61M 2005/208* (2013.01); *A61M 2005/2073* (2013.01); *A61M 2005/323* (2013.01); *A61M 2005/3223* (2013.01); *A61M 2005/3224* (2013.01); *A61M 2005/3226* (2013.01); *A61M 2005/3228* (2013.01); *A61M 2005/3235* (2013.01); *A61M 2005/3236* (2013.01); *A61M 2005/3239* (2013.01); *A61M 2005/3241* (2013.01)

(58) Field of Classification Search
CPC ........ A61M 5/3232; A61M 2005/2073; A61M 2005/208; A61M 2005/3223; A61M 2005/3224; A61M 2005/3226; A61M 2005/3228; A61M 2005/3235; A61M 2005/3236; A61M 2005/323; A61M 2005/3239; A61M 2005/3241
See application file for complete search history.

(56) References Cited

U.S. PATENT DOCUMENTS

| | | | |
|---|---|---|---|
| 2,866,458 A | 12/1958 | Hein, Jr. | |
| 3,094,988 A | 6/1963 | Dunmire | |
| 3,280,465 A | 10/1966 | Dolgorukov | |
| 3,797,491 A | 3/1974 | Hurschman | |
| 4,373,535 A | 2/1983 | Martell | |
| 4,553,962 A * | 11/1985 | Brunet | A61M 5/2033 604/198 |
| 4,592,745 A | 6/1986 | Rex et al. | |
| 4,682,980 A | 7/1987 | Suzuki | |
| 4,894,055 A | 1/1990 | Sudnak | |
| 4,961,728 A | 10/1990 | Kosinski | |
| 4,973,310 A | 11/1990 | Kosinski | |
| 4,988,339 A | 1/1991 | Vadher | |
| 5,007,903 A | 4/1991 | Ellard | |
| 5,053,010 A | 10/1991 | McGary et al. | |
| 5,167,641 A | 12/1992 | Schmitz | |
| 5,205,820 A | 4/1993 | Kriesel | |
| 5,222,948 A | 6/1993 | Austin et al. | |
| 5,226,896 A | 7/1993 | Harris | |
| 5,267,963 A | 12/1993 | Bachynsky | |
| 5,358,489 A | 10/1994 | Wyrick | |
| 5,385,551 A | 1/1995 | Shaw | |
| 5,387,195 A * | 2/1995 | Hicks | A61M 5/5013 604/110 |
| 5,514,097 A | 5/1996 | Knauer | |
| 5,637,087 A | 6/1997 | O'Neil et al. | |
| 5,938,637 A | 8/1999 | Austin et al. | |
| 5,961,491 A | 10/1999 | McGarry et al. | |
| 5,971,964 A | 10/1999 | Donaldson | |
| 6,015,438 A | 1/2000 | Shaw | |
| 6,086,566 A | 7/2000 | Amissolle | |
| 6,102,896 A | 8/2000 | Roser | |
| 6,126,637 A | 10/2000 | Kriesel | |
| 6,186,980 B1 | 2/2001 | Brunel | |
| 6,409,701 B1 | 6/2002 | Cohn et al. | |
| 6,494,863 B1 | 12/2002 | Shaw et al. | |
| 6,565,540 B1 | 5/2003 | Perouse | |
| 6,572,584 B1 | 6/2003 | Shaw et al. | |
| 6,699,218 B2 | 3/2004 | Flaherty et al. | |
| 6,736,070 B2 | 5/2004 | Baltos | |
| 6,796,965 B2 | 9/2004 | Dumaresq-Lucas et al. | |
| 7,014,622 B1 | 3/2006 | Pressly, Sr. et al. | |
| RE39,107 E | 5/2006 | Shaw | |
| 7,056,306 B1 | 6/2006 | Halseth et al. | |
| 7,101,351 B2 | 9/2006 | Crawford et al. | |
| 7,258,678 B2 | 8/2007 | Wilkinson | |
| 7,344,517 B2 | 3/2008 | Schiller | |
| 7,429,256 B2 | 9/2008 | Chevallier et al. | |
| 7,468,054 B2 | 12/2008 | Crawford et al. | |
| 7,488,308 B2 | 2/2009 | Lesch, Jr. | |
| 7,670,314 B2 | 3/2010 | Wall et al. | |
| 7,699,813 B2 | 4/2010 | Liversidge | |
| 7,717,877 B2 | 5/2010 | Lavi et al. | |
| 7,918,821 B2 | 4/2011 | Mahurkar | |
| 7,935,087 B2 | 5/2011 | Judd et al. | |
| 7,963,949 B2 | 6/2011 | Chevallier et al. | |
| 7,976,499 B2 | 7/2011 | Grunhut et al. | |
| 7,988,663 B2 | 8/2011 | Schiller et al. | |
| 8,002,745 B2 | 8/2011 | Kaal et al. | |
| 8,021,333 B2 | 9/2011 | Kaal et al. | |
| 8,114,050 B2 | 2/2012 | Kaal et al. | |
| 8,114,051 B2 | 2/2012 | Walsh et al. | |
| 8,167,837 B2 | 5/2012 | Judd et al. | |
| 8,231,571 B2 | 7/2012 | Chevallier et al. | |
| 8,235,967 B2 | 8/2012 | Chevallier et al. | |
| 8,361,018 B2 | 1/2013 | Caizza et al. | |
| 8,361,035 B2 | 1/2013 | Thorley et al. | |
| 8,419,682 B2 | 4/2013 | Woehr et al. | |
| 8,574,214 B2 | 11/2013 | Kuhn et al. | |
| 8,617,105 B2 | 12/2013 | Chevallier et al. | |
| 8,636,688 B2 | 1/2014 | Shaw | |
| 8,696,628 B2 | 4/2014 | Grunhut | |
| 8,708,975 B2 | 4/2014 | Heald | |
| 8,728,042 B2 | 5/2014 | Pickhard | |
| 8,790,302 B2 | 7/2014 | Wayman et al. | |
| 8,790,313 B2 | 7/2014 | Thorley | |
| 8,801,673 B2 | 8/2014 | Zaiken et al. | |
| 8,911,401 B2 | 12/2014 | Roberts et al. | |
| 9,044,553 B2 | 6/2015 | James et al. | |
| 9,061,106 B2 | 6/2015 | Roberts et al. | |
| 9,155,844 B2 | 10/2015 | Brereton et al. | |
| 9,174,007 B2 | 11/2015 | Lum et al. | |
| 9,180,258 B2 | 11/2015 | Kemp et al. | |
| 2003/0236500 A1 | 12/2003 | Scheu | |
| 2009/0093759 A1 | 4/2009 | Judd | |
| 2010/0280460 A1 * | 11/2010 | Markussen | A61M 5/2033 604/195 |
| 2011/0178501 A1 | 7/2011 | Clearthero | |
| 2011/0224640 A1 | 9/2011 | Kuhn et al. | |
| 2012/0022466 A1 | 1/2012 | James et al. | |
| 2012/0041379 A1 | 2/2012 | Macarthur et al. | |
| 2012/0074001 A1 | 3/2012 | Genosar | |
| 2012/0101448 A1 | 4/2012 | Jiang | |
| 2012/0130340 A1 | 5/2012 | Knutson | |
| 2012/0316466 A1 | 12/2012 | Crawford et al. | |
| 2013/0035664 A1 | 2/2013 | Mojdehbakhsh et al. | |
| 2013/0060191 A1 | 3/2013 | Thorley et al. | |
| 2013/0060202 A1 | 3/2013 | Thorley et al. | |
| 2013/0079716 A1 | 3/2013 | Thorley et al. | |
| 2013/0102973 A1 | 4/2013 | Thorley et al. | |
| 2014/0303564 A1 | 10/2014 | Roberts et al. | |
| 2014/0336582 A1 | 11/2014 | Tisci et al. | |

FOREIGN PATENT DOCUMENTS

| | | |
|---|---|---|
| DE | 102004055870 | 5/2006 |
| DE | 102007056759 | 5/2009 |
| FR | 2686022 A1 | 7/1993 |
| JP | H2-500340 A | 2/1990 |
| JP | H6-142204 A | 12/1995 |
| JP | 2008073237 A | 4/2008 |
| WO | 9921609 A1 | 5/1999 |
| WO | 2004050136 | 6/2004 |
| WO | 2008133702 | 11/2008 |
| WO | 2012059449 | 5/2010 |

OTHER PUBLICATIONS

Chinese Office Action issued in Chinese Application No. 201380068939.5, dated Dec. 18, 2017.

(56) References Cited

OTHER PUBLICATIONS

Japanese Office Action issued in Japanese Application No. 2015-541255, dated Aug. 28, 2017.
Japanese Office Action issued in Japanese Application No. 2018-035544, dated Feb. 20, 2019.
Russian Office Action issued in Russian Application No. 2015121943, dated Oct. 31, 2017.

* cited by examiner

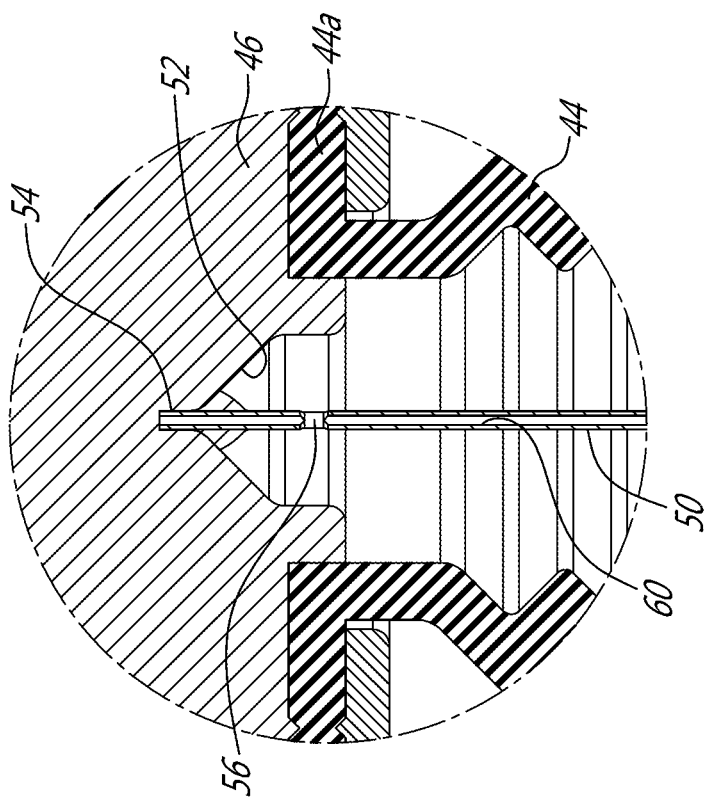
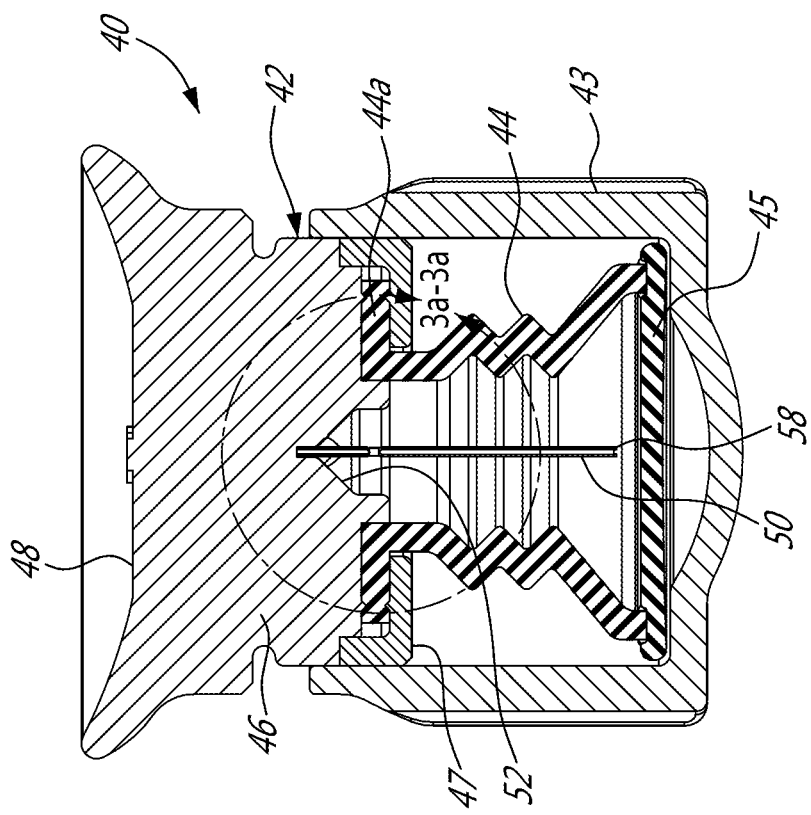
FIG. 3A
FIG. 3

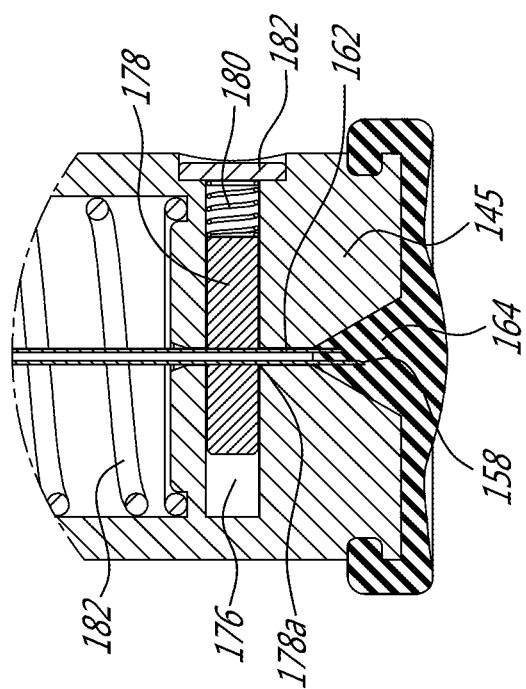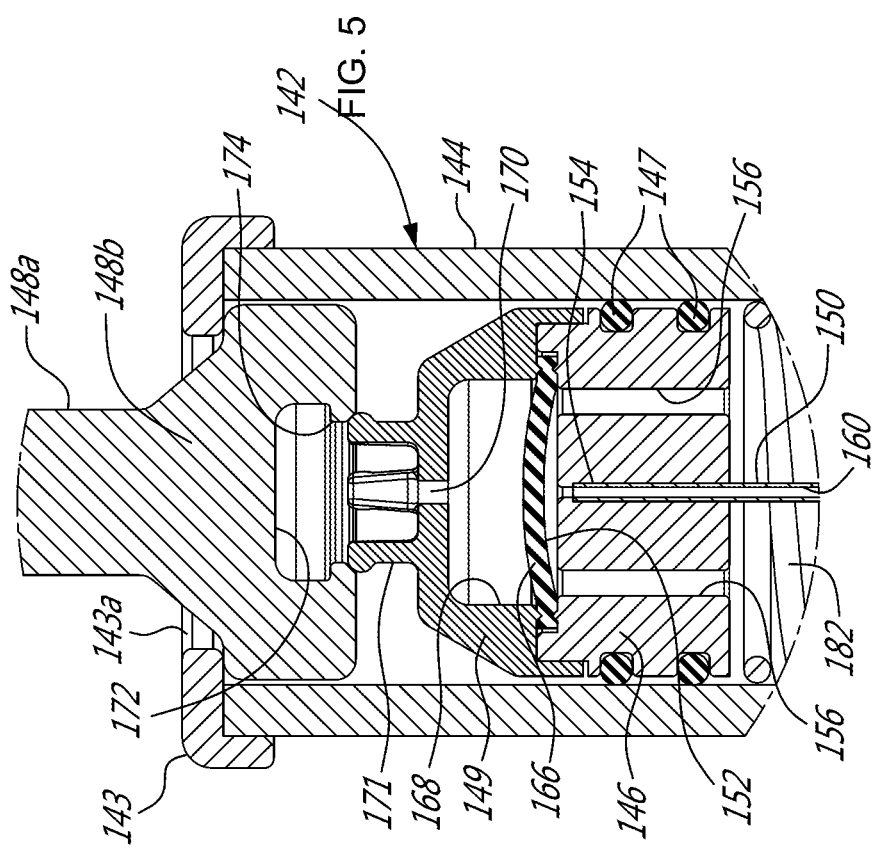

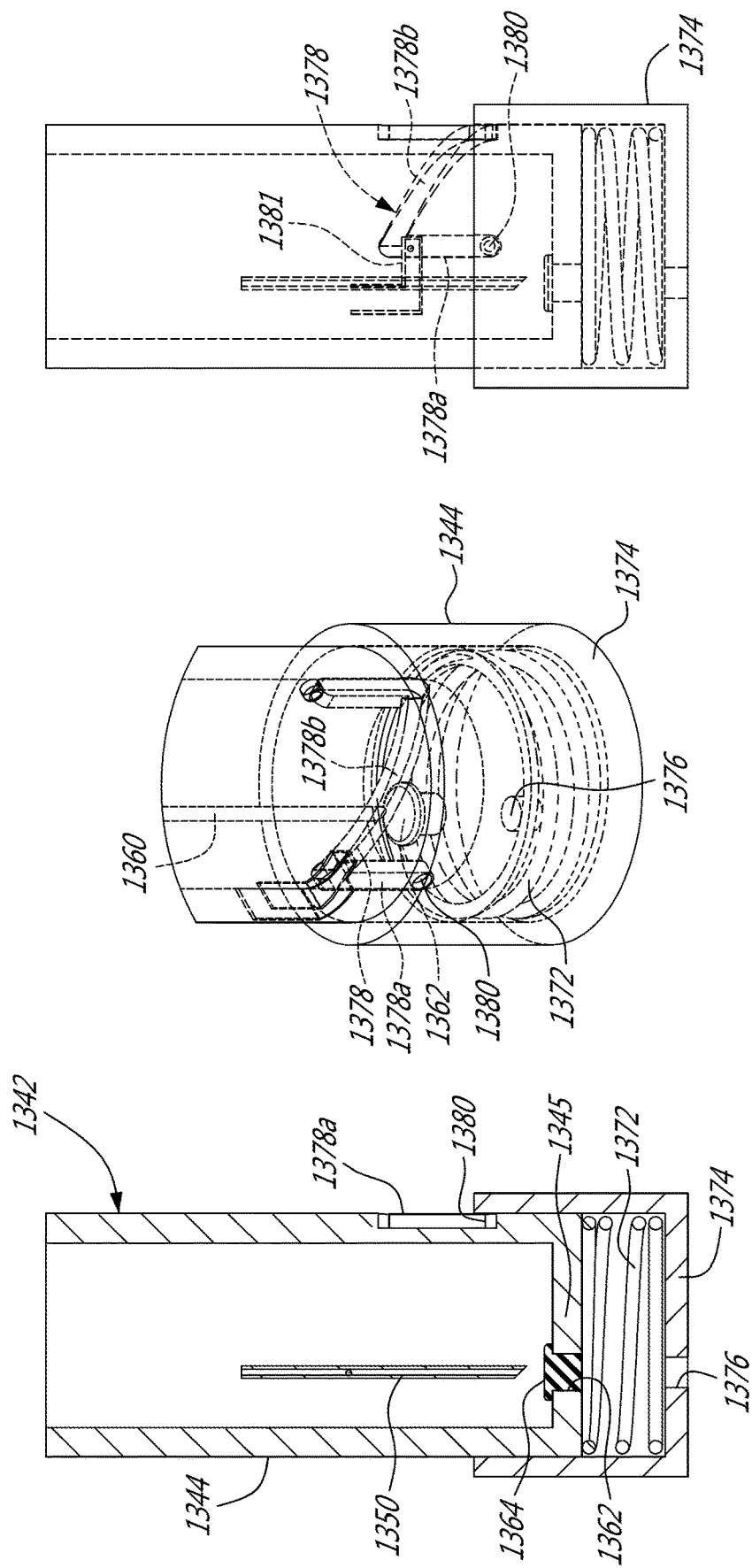

FLUID DELIVERY DEVICE AND METHOD

TECHNICAL FIELD

The described subject matter relates generally to fluid delivery devices and more particularly to a medical, transcutaneous fluid delivery injector.

BACKGROUND ART

Conventional syringes, including hypodermic as well as other types of syringes, typically have fixed needles which protrude forwardly from the end of the syringe barrel. In a hypodermic syringe, the barrel contains the medication used in an injection. In transport of the syringe, and in storage prior to actual use, syringe needles are typically protected in some fashion, such as by an elongated plastic cap which fits around the needle. Further, the entire syringe is sometimes encased in a paper or plastic container. These packaging techniques insure the sterility of the syringe, but also serve to protect the clinician or other user of the syringe from accidentally getting nicked or pricked by the syringe needle, a result generally referred to as a needle "stick".

Syringes are normally handled by trained professionals is a hospital or clinic and therefore "stick" is less likely to occur. However delivery of some medicines in the field, especially in emergency situations, may not be done by trained professionals.

Risk of infection, such as for hepatitis, the AIDS virus, and in particular the severity of the effects thereof and the knowledge that the virus can be transmitted by needles, has created an extraordinary concern over the possibility of needle sticks.

There exists retractable needles, but these are generally of the type for drawing blood samples. Syringes that have a retracted needle before and/or after use are mainly expensive with complicated mechanical structures.

Accordingly, there is a need to provide a fluid delivery device that is simple, inexpensive and safe.

SUMMARY

In one aspect, the invention is a fluid delivery injector comprising: a syringe having a barrel with a peripheral wall having a longitudinal axis and a distal end wall; a plunger movable within the barrel parallel to the longitudinal axis towards and away from the end wall; at least one hollow needle anchored at its proximal end to the plunger and extending parallel to the axis towards the end wall with the needle contained within the barrel; a fluid retention reservoir defined in at least the barrel. The hollow needle has an inlet port adjacent the proximal end, upstream of the reservoir, and a discharge port is at the distal end thereof. The fluid retention reservoir is in fluid communication with the needle when a volume confining pressure is applied to the fluid and the needle is projected beyond the end wall of the barrel simultaneously as the pressure is applied to the plunger in the direction of the distal end wall.

In a more specific embodiment, an energy storage device is provided within the syringe for retaining the plunger in a default position spaced from the end wall with the at least one hollow needle contained within the barrel and for returning the needle to the default position once the pressure is released from the plunger.

In a yet more specific embodiment the subject matter relates to a transcutaneous fluid injector. In this specific embodiment, the injector is particularly suitable for administering a single dose or multiple doses simultaneously of a drug, such as a vaccine, where needle stick is avoided since the needle projects from the syringe only when a one-time pressure is applied to project the needle into the patient.

In another aspect of the present invention, a fluid delivery injector comprises a syringe having a peripheral wall defining a barrel with a longitudinal axis; a plunger provided within the barrel adapted for linear movement parallel to the longitudinal axis; at least one hollow needle anchored at its proximal end to the plunger and extending parallel to the axis; a fluid retention reservoir defined in at least one of the barrel and plunger and in fluid communication with the needle when a volume confining pressure is applied to the fluid; and the reservoir including at least an energy storing portion for providing the volume confining pressure to the fluid.

In yet another aspect of the present invention, a retractable needle assembly comprises a syringe including a rigid cylindrical barrel having an end wall with an opening for passing a needle; a plunger and needle unit are adapted to move axially within the barrel for passing the needle through the opening in the end wall; means for retracting the needle from a position with the needle projecting beyond the end wall to a position with the needle retracted within the barrel clear of the end wall; the improvement comprising a needle blocking device associated with the end wall and including at least one sliding member adapted to cross the opening in the end wall when the needle is retracted and clear of the opening.

In accordance with an aspect of the present invention there is method for injecting at least a dose of a fluid medication transcutaneously into the body with the use of a syringe that includes a barrel, a plunger mounting a hollow needle and a fluid retention reservoir within the syringe; the method comprising the steps of maintaining the needle contained within the barrel, pressing the distal end of the barrel against the skin of a patient; applying pressure to the plunger and the fluid retention reservoir to project the needle beyond the barrel and to pierce the skin of the patient; simultaneously transferring the fluid from the reservoir through the hollow needle and into the patient.

In accordance with one aspect of the present invention, there is provided A fluid delivery injector comprising: a syringe having: a barrel with a peripheral wall having a longitudinal axis and a distal end wall; a plunger movable with the barrel parallel to the longitudinal axis towards and away from the end wall; at least one hollow needle anchored at its proximal end to the plunger and extending parallel to the axis towards the end wall with the needle contained within the barrel; a fluid retention reservoir defined in at least the barrel the fluid retention reservoir in fluid communication with inlet port of the needle when a volume confining pressure is applied to the fluid; whereby the needle is projected beyond the end wall of the barrel only when pressure is applied to the plunger in the direction of the distal end wall.

In accordance with one aspect of the fluid delivery injector herein described, wherein an energy storage device is provided within the syringe for retaining the plunger in a default position spaced from the end wall with the at least one hollow needle contained within the barrel and for returning the needle to the default position once the pressure is released from the plunger.

In accordance with another aspect of the fluid delivery injector herein described, wherein the peripheral wall of the barrel is a collapsible energy storing material.

In accordance with yet another aspect of the fluid delivery injector herein described, wherein the end wall is provided with a pierceable septum for sealingly engaging the needle.

In accordance with still another aspect of the fluid delivery injector herein described, wherein the syringe is provided with a press member of rigid material at the proximal end of the barrel associated with the plunger.

In accordance with yet still aspect of the fluid delivery injector herein described, wherein fluid retention reservoir is defined in the barrel while the needle is provided with at least an inlet port at the proximal end of the needle communicating the hollow bore of the needle with the fluid in the reservoir.

In accordance with a further aspect of the fluid delivery injector herein described, wherein the peripheral wall of the barrel is an elastomeric material adapted to store energy whereby the volume confining pressure applied to the fluid is provided manually through the plunger and the elastomeric wall of the barrel.

In accordance with yet a further aspect of the fluid delivery injector herein described, wherein the end wall is a material suitable for a pierceable septum and the needle sealingly engages the end wall.

In accordance with still a further aspect of the fluid delivery injector herein described, wherein the plunger is of rigid material and defines a recess surrounding part of the base of the needle where inlet ports are located.

In accordance with yet still a further aspect of the fluid delivery injector herein described, wherein the elastomeric peripheral wall is in the form of an accordion, that is expandable laterally, and a rigid cap engages and covers the barrel when not in use.

In accordance with one embodiment of the fluid delivery injector herein described, wherein the peripheral wall of the barrel is a rigid cylinder and the plunger slides along the axis in sealing contact with the peripheral wall.

In accordance with another embodiment of the fluid delivery injector herein described, wherein the plunger includes a closed cavity with an elastomeric membrane forming an expandable chamber in communication with the hollow needle and the fluid retention reservoir is formed within the barrel between the plunger and the end wall and is in communication with the expandable chamber through conduits defined in the plunger.

In accordance with yet another embodiment of the fluid delivery injector herein described, wherein the plunger includes a recess concentric with the axis of the needle and an elastomeric membrane is provided in the recess while the fluid retention reservoir is formed within the barrel between the end wall and the membrane in the recess; and at least an inlet port is provided near the proximal end of the needle in communication with the reservoir and the hollow bore of the needle whereby when pressure is applied to the plunger the needle projects beyond the end wall and the fluid, on the urging of the membrane, passes into the needle.

In accordance with still another of the fluid delivery injector herein described, wherein an elastomeric membrane is fixed to a proximal end of the barrel and extends concentrically with the axis of the needle; a rigid sleeve is fixed to the proximal end of the barrel and extends axially within and concentric to the membrane while the plunger slides within and is sealed to the sleeve; and the fluid retaining reservoir is within the membrane confined by the plunger.

In accordance with yet still another embodiment of the fluid delivery injector herein described, wherein the plunger is made of an elastomer and defines a closed cavity, within the barrel, that forms the fluid retention reservoir and is in fluid communication with the hollow needle.

In accordance with a further embodiment of the fluid delivery injector herein described, wherein the energy storing device includes a coil spring in the barrel between the end wall and the plunger for returning the plunger to its default position with the needle retracted into the barrel when pressure is released from the press member.

In accordance with yet a further embodiment of the fluid delivery injector herein described, wherein a second fluid retention reservoir is formed within the barrel between the plunger and the end wall and at least a secondary needle extends through the end wall and is in communication with the second reservoir; an elastomeric bellows extends from the distal portion of the end wall defining a closed cavity and a second end wall in which the at least secondary needle is contained whereby separate liquid doses are retained within the first and second reservoirs respectively whereby when pressure is applied to the press member the needle and the at least secondary needle project beyond the end wall and the bellows to administer the separate liquids to the patient.

In accordance with still a further embodiment of the fluid delivery injector herein described, wherein the plunger is an elastomeric sleeve with a distal end wall and the press member is a rigid block inserted in the sleeve but spaced from the plunger distal end wall to form a cavity as an expansion chamber in communication with the hollow needle; the fluid retention reservoir is formed within the barrel between the end wall of the barrel and the plunger distal end wall; at least one bore extending through the plunger distal end wall in communication with the reservoir and the expansion chamber such that when pressure is applied to the press member the fluid will flow from the reservoir through the expansion chamber into the needle as the needle projects through the end wall of the barrel into the patient.

In accordance with yet still a further embodiment of the fluid delivery injector herein described, wherein the energy storage device is the elastomeric sleeve connected to and extending between the proximal end of the barrel and the plunger in order to retract the plunger and the needle when pressure is released from the plunger so that the needle is within the confines of the barrel.

In accordance with another aspect of the fluid delivery injector herein described, wherein the plunger is an elastomeric sleeve with a distal end wall and the press member is a rigid block inserted in the sleeve but spaced from the plunger distal end wall to form a cavity as an expansion chamber in communication with the hollow needle; a conical bellows is provided within the barrel extending from the end wall concentrically with the axis of the needle such that the bellows defines the reservoir within the barrel and the plunger distal end wall and provides the volume confining pressure to the fluid in the reservoir.

In accordance with yet another aspect of the fluid delivery injector herein described, wherein the energy storing device for retracting the plunger and needle includes an elastomeric annular accordion member surrounding the conical bellows.

In accordance with still another aspect of the fluid delivery injector herein described, wherein the plunger is integral with the press member and is a rigid cylinder movable in sliding contact with the barrel; an elastomeric bellows is concentric with the needle in sealing engagement with the end wall at the base thereof and the distal portion of the plunger at the apex thereof, defining the fluid retention reservoir; and the needle having an inlet port near the proximal end of the needle communicating the reservoir with the hollow needle whereby when pressure is applied to the press member the fluid will flow from the reservoir through the needle as the needle projects beyond the end wall of the barrel.

In accordance with yet still another aspect of the fluid delivery injector herein described, wherein the plunger is in the form of an elastomeric sleeve with a distal end wall and a second sleeve, having a pierceable distal end wall, provided for axial sliding movement within the elastomeric sleeve and defining a first cavity between the elastomeric sleeve and the second sleeve; a press member engaging the second sleeve for forming a sealed second cavity therewith; the needle being anchored in the elastomeric sleeve distal end wall at the proximal end of the needle and a portion of the proximal end of the needle protruding into the first cavity with the distal end of the needle projecting towards the end wall of the barrel; at least a secondary needle communicating with the barrel and anchored in the elastomeric distal end wall but extending into the first cavity; a first fluid retention reservoir formed in the barrel between the barrel end wall and the elastomeric distal end wall in communication with the secondary needle; a mixing chamber formed in the second cavity adapted to contain a separate component; the at least secondary needle in communication with the first reservoir whereby when pressure is applied to the press member, the second sleeve will move axially within the elastomeric sleeve and the needle as well as the secondary needle will pierce the pierceable end wall of the second sleeve and as the plunger continues its axial movement the fluid from the first reservoir enters the mixing chamber to form a solution with the second component and the solution flows into the hollow needle while the hollow needle projects through the barrel end wall.

In accordance with another aspect of the present invention, there is provided a fluid delivery injector for injecting a solution mixed from at least two components, at least one of which is a liquid, the injector comprising a syringe including: a barrel with a closed end wall; a plunger; and a first needle anchored at a proximal end to the plunger to be axially slidable within the barrel; wherein the plunger is in the form of an elastomeric sleeve with a distal end wall; and a second sleeve having a pierceable distal end wall, provided for axial sliding movement within the elastomeric sleeve and defining a first cavity between the elastomeric sleeve and the second sleeve; a press member engaging the second sleeve for forming a sealed second cavity therewith; the first needle having a portion protruding into the first cavity; at least a secondary needle anchored in the elastomeric distal end wall and extending into the first cavity; a first fluid retention reservoir formed in the barrel between the barrel end wall and the elastomeric distal end wall; and a mixing chamber formed in the second cavity adapted to contain a separate component; the at least secondary needle in communication with the first reservoir; whereby when pressure is applied to the press member and thus the plunger, the second sleeve will move axially within the elastomeric sleeve causing the first needle as well as the secondary needle to pierce the pierceable end wall of the second sleeve and as the plunger continues its axial movement the fluid from the first reservoir enters the mixing chamber to form a solution with the second component and the solution flows into the first needle while the first needle projects through the barrel end wall.

In accordance with a further aspect of the fluid delivery injector herein described, wherein the end wall includes a device for blocking the travel of the needle, once the needle has been retracted, including a transverse bore intersecting the axis of the needle, a shuttle adapted for sliding movement along the bore with a shuttle bore for the passage of the needle when the needle is in a position within the barrel prior to delivering a liquid, and a spring in the bore urging the shuttle to a position with the shuttle bore misaligned with the needle when the needle has been retracted after delivery of the liquid.

In accordance with yet a further aspect of the fluid delivery injector herein described, wherein the end wall includes a device for blocking the travel of the needle, once the needle has been retracted, the device including: a rigid cap mounted for movement on the distal end of the barrel and including a cam track defined on one of the inner surface of the cap and the outer surface of the barrel and a cam follower on the other of the surfaces; an energy storage device within the cap and the barrel end wall; an opening defined in the cap axially aligned with the needle when the injector is in the default position, whereby the energy storage device is compressed when pressure is applied to project the needle from the opening in the cap, and when the pressure is removed, the energy storage device distends causing an interaction of the cam follower and the cam track to misalign the opening in the cap with the needle when the needle has been retracted.

In accordance with still a further aspect of the fluid delivery injector herein described, wherein the press member defines a recess having an axis coextensive with the axis of the barrel and the proximal end of the plunger has snap fingers parallel to the axis such that when the pressure is applied to the press member the snap fingers move into and engage the recess such that the overall length of the press member, plunger and needle is shorter causing the needle to retract to the extent that the needle is clear of the transverse bore when the needle is retracted.

In accordance with yet still another aspect of the fluid delivery injector herein described, wherein the fluid is a liquid.

In accordance with another embodiment of the fluid delivery injector herein described, wherein liquid is medicinal liquid.

In accordance with yet another embodiment of the fluid delivery injector herein described, wherein the medicinal liquid is a vaccine.

In accordance with yet another aspect of the present invention, there is provided a fluid delivery injector comprising a syringe having a peripheral wall defining a barrel with a longitudinal axis; a plunger provided within the barrel adapted for linear movement parallel to the longitudinal axis; at least one hollow needle anchored at its proximal end to the plunger and extending parallel to the axis; a fluid retention reservoir defined in at least the barrel and in fluid communication with the needle when a volume confining pressure is applied to the fluid; and the reservoir including at least an energy storing portion for providing the volume confining pressure to the fluid.

In accordance with still another embodiment of the fluid delivery injector herein described, wherein the hollow needle has an inlet port adjacent the proximal end thereof and the fluid communication between the reservoir and the hollow needle is through the inlet port.

In accordance with yet still another embodiment of the fluid delivery injector herein described, wherein the peripheral wall of the barrel is an elastomeric material adapted to store energy whereby the volume confining pressure applied to the fluid is provided manually through the plunger and the elastomeric wall of the barrel.

In accordance with a further embodiment of the fluid delivery injector herein described, wherein the barrel includes a rigid peripheral cylindrical wall and an end wall and the plunger slides along the axis in sealing contact with the peripheral wall; the plunger includes a closed cavity with an elastomeric membrane forming an expandable chamber in communication with the hollow needle and the fluid retention reservoir is formed within the barrel between the plunger and the end wall and is in communication with the expandable chamber through conduits defined in the plunger.

In accordance with yet a further embodiment of the fluid delivery injector herein described, wherein the barrel has a rigid peripheral cylindrical wall and an end wall; the plunger includes a recess concentric with the axis of the needle and an elastomeric membrane is provided in the recess while the fluid retention reservoir is formed within the barrel between the end wall and the membrane in the recess.

In accordance with yet a further embodiment of the fluid delivery injector herein described, wherein the barrel has a rigid peripheral cylindrical wall; an elastomeric membrane is fixed to a proximal end of the barrel and extends concentrically with the axis of the needle; a rigid sleeve is fixed to the proximal end of the barrel and extends axially within and concentric to the membrane while the plunger slides within and is sealed to the sleeve; and the fluid retaining reservoir is within the membrane confined by the plunger.

In accordance with still another aspect of the present invention, there is provided a retractable needle assembly comprising a syringe including a rigid cylindrical barrel having an end wall with an opening for passing a needle; a plunger and needle unit adapted to move axially within the barrel and the needle through the opening in the end wall; means for retracting the needle from a position with the needle projecting beyond the end wall to a position with the needle retracted within the barrel clear of the end wall; the improvement comprising a needle blocking device associated with the end wall and including at least one sliding member adapted to cross the opening in the end wall when the needle is retracted and clear of the opening.

In accordance with another aspect of the fluid delivery injector herein described, wherein the blocking device includes a transverse bore defined in the end wall intersecting the axis of the needle, a shuttle adapted for sliding movement along the bore with a shuttle bore for the passage of the needle when the needle is in a position within the barrel prior projecting from the barrel, and a spring in the bore urging the shuttle to a position with the shuttle bore misaligned with the needle when the needle has been retracted.

In accordance with yet another aspect of the fluid delivery injector herein described, wherein the blocking device includes a rigid cap mounted for movement on the distal end of the barrel and including a cam track defined on one of the inner surface of the cap and the outer surface of the barrel and a cam follower on the other of the surfaces; an energy storage device within the cap and the barrel end wall; an opening defined in the cap axially aligned with the needle when the injector is in the default position, whereby the energy storage device is compressed when pressure is applied to project the needle from the opening in the cap, and when the pressure is removed, the energy storage device distends causing an interaction of the cam follower and the cam track to misalign the opening in the cap with the needle when the needle has been retracted.

In accordance with yet still another aspect of the present invention, there is provided a method for injecting at least a dose of a fluid medication transcutaneously into the body with the use of a syringe that includes a barrel, a plunger mounting a hollow needle having a proximal inlet port adjacent the plunger and a fluid retention reservoir within the barrel, comprising the steps of maintaining the needle contained within the barrel, pressing the distal end of the barrel against the skin of a patient; applying pressure to the plunger and the fluid retention reservoir to project the needle beyond the barrel and to pierce the skin of the patient; and transferring the fluid from the reservoir through the inlet port of hollow needle and into the patient.

In accordance with still another aspect of the fluid delivery injector herein described wherein the fluid moves in a direction counter to the direction of the plunger to pass the fluid through the inlet port when the pressure is applied to the retention reservoir.

In accordance with yet still another aspect of the fluid delivery injector herein described, including the further step of releasing the pressure on the plunger whereby the plunger is retracted and the needle is returned to being contained within the barrel.

In accordance with yet another aspect of the fluid delivery injector herein described, comprising pre-loading the medicinal fluid into the fluid retention reservoir, prior to use.

In accordance with still another aspect of the fluid delivery injector herein described, wherein the plunger is a hollow compressible elastomeric fluid retention reservoir and the medicinal fluid is pre-loaded into the reservoir before use.

For clarity the following terms are explained in more detail:

"Volume confining pressure" is any device which may apply pressure to the fluid in the reservoir such as an elastomeric energy storage wall forming part of the reservoir; a portion of the reservoir wall that may move under pressure to reduce the volume of the reservoir such as a plunger. The description mentions a membrane, for instance, that may be stretched when pressure is applied by the plunger. The membrane stores the energy which is then released thus applying pressure to the fluid to move the liquid through the needle.

"A press member" is a device engaeable by manually by a thumb or by through a mechanical device to apply pressure to the plunger or expansion chamber associated with the reservoir.

"Sealingly engaging the needle" refers to a device such as the septum in which the needle may be embedded before use, and through which the needle will pass when the needle is deployed.

"Septum is used to denote the barrier of pierceable material closing any opening at the end of the syringe barrel but pierceable when the hollow needle is being projected beyond the barrel.

"Anchored" means that the needle is fixed at or near is proximal end such that the needle will travel only with the plunger.

BRIEF DESCRIPTION OF THE DRAWINGS

Reference is now made to the accompanying figures in which:

FIG. 3 is a longitudinal cross section taken through lines 3-3 of FIG. 2;

FIG. 3a is an enlarged fragmentary cross section of a detail shown in FIG. 3;

FIG. 6a is an enlarged fragmentary cross section of a detail shown in FIG. 6;

FIG. 6b is an enlarged fragmentary cross section of a further detail shown in FIG. 6;

FIG. 24 is a longitudinal cross section taken though part of an injector showing an embodiment of a detail thereof;

FIG. 25 is a fragmentary, perspective view showing the embodiment of FIG. 24;

FIG. 25a is a schematic elevation showing the operation of the detail in FIG. 25;

DESCRIPTION OF THE PREFERRED EMBODIMENTS

Figure 2:
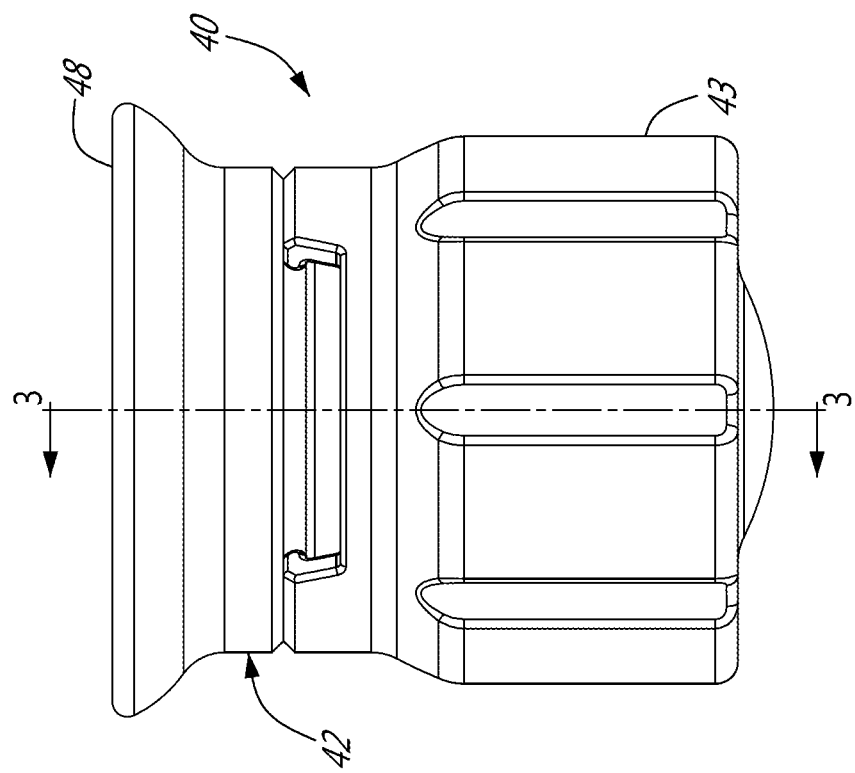
FIG. 2 is an elevation view of the injector shown in FIG. 1.
Figure 1:
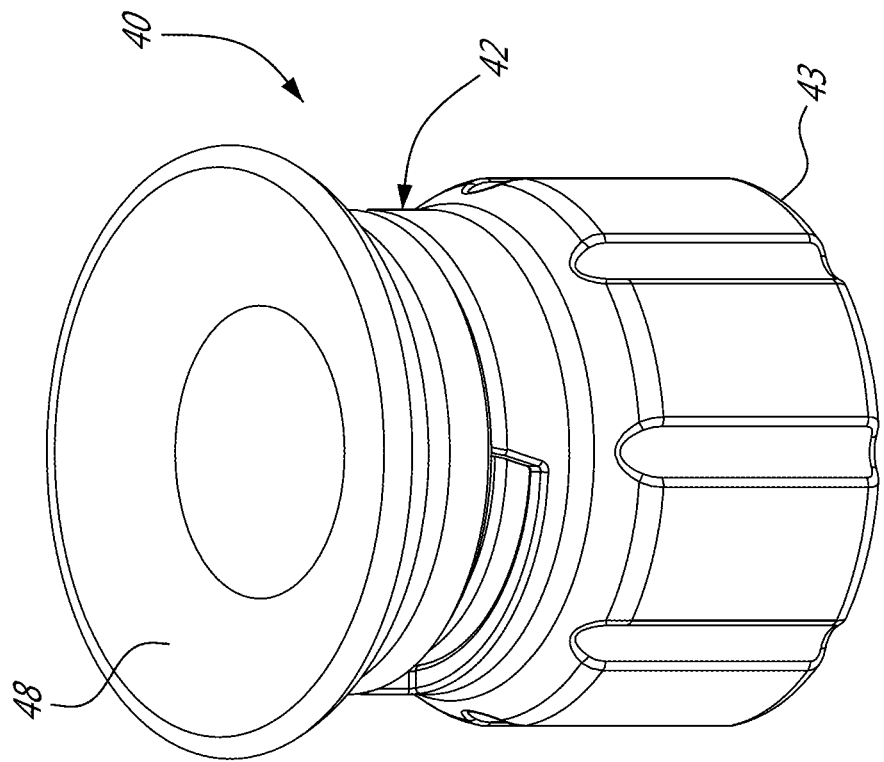
FIG. 1 is a perspective view of an embodiment of an injector.

An embodiment of a transcutaneous injector 40 is illustrated in FIGS. 1 to 3. The injector 40 includes a syringe 42 covered by a cylindrical cap 43. The syringe 42 includes a barrel 44 with an end wall 45. A press block 48 is fixed to the other end of the barrel 44. A hollow needle 50, completely enclosed within the barrel 44 is anchored at its base 54 to the press block 48.

The press block 48 may be made of polycarbonate or other similar material. The proximal end of the press block has a shallow concave surface adapted to receive the thumb of the person administering the injection. As shown in FIGS. 3 and 3a, the distal end of the press block 48 forms the plunger 46. The plunger includes a recess forming a expansion chamber 52 surrounding the needle 50. The needle 50 may be a 27 gauge needle or slightly larger and defines a bore 60 communicating with ports 56 defined in the wall of the needle 50, confined within the expansion chamber 52. The distal end of the needle 50 is a sharpened tip 58.

The barrel 44 is in the form of a collapsible accordion with an proximal flange 44a held to the plunger 46 by means of a retaining collar 47. In one example, the material forming the barrel 44 is a silicone KE-2000 having a shore A hardness of 80. The distal end of the barrel 44 is connected to the end wall 45. The end wall 45, for the purposes of the present embodiment, is referred to as a septum that is pierceable by the needle 50. Typically the material of the end wall 45 could be a silicone KE 2000 having a shore A hardness of 60. The barrel 44 as described forms a reservoir for the fluid to be delivered. Any similar medical grade elastomer may be used for the barrel and the end wall.

Figure 4:
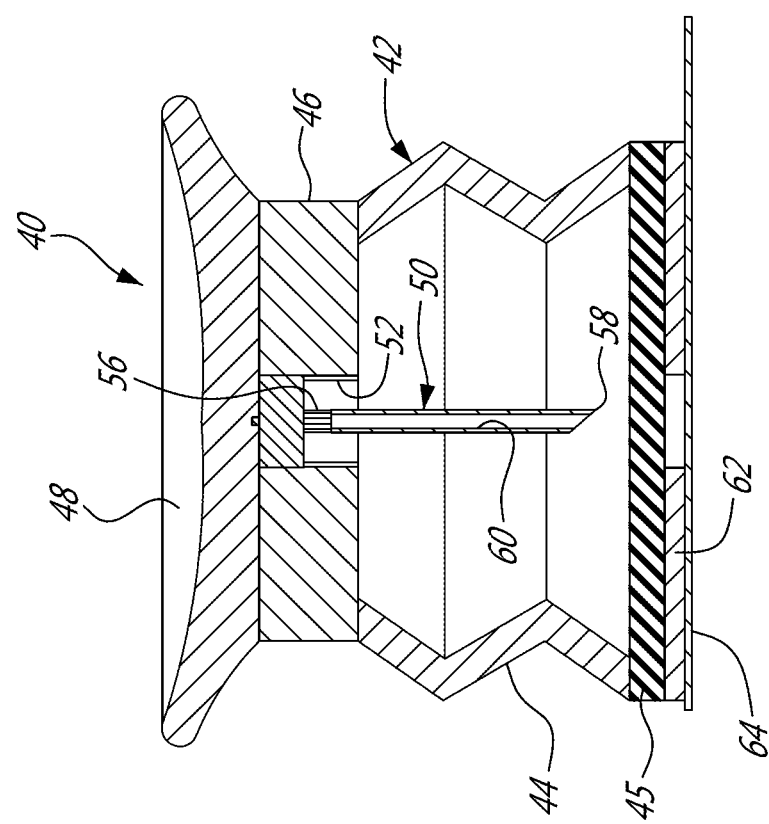
FIG. 4 is a schematic longitudinal cross section based on the embodiment shown in FIG. 3, showing an additional feature.
Figure 4A:
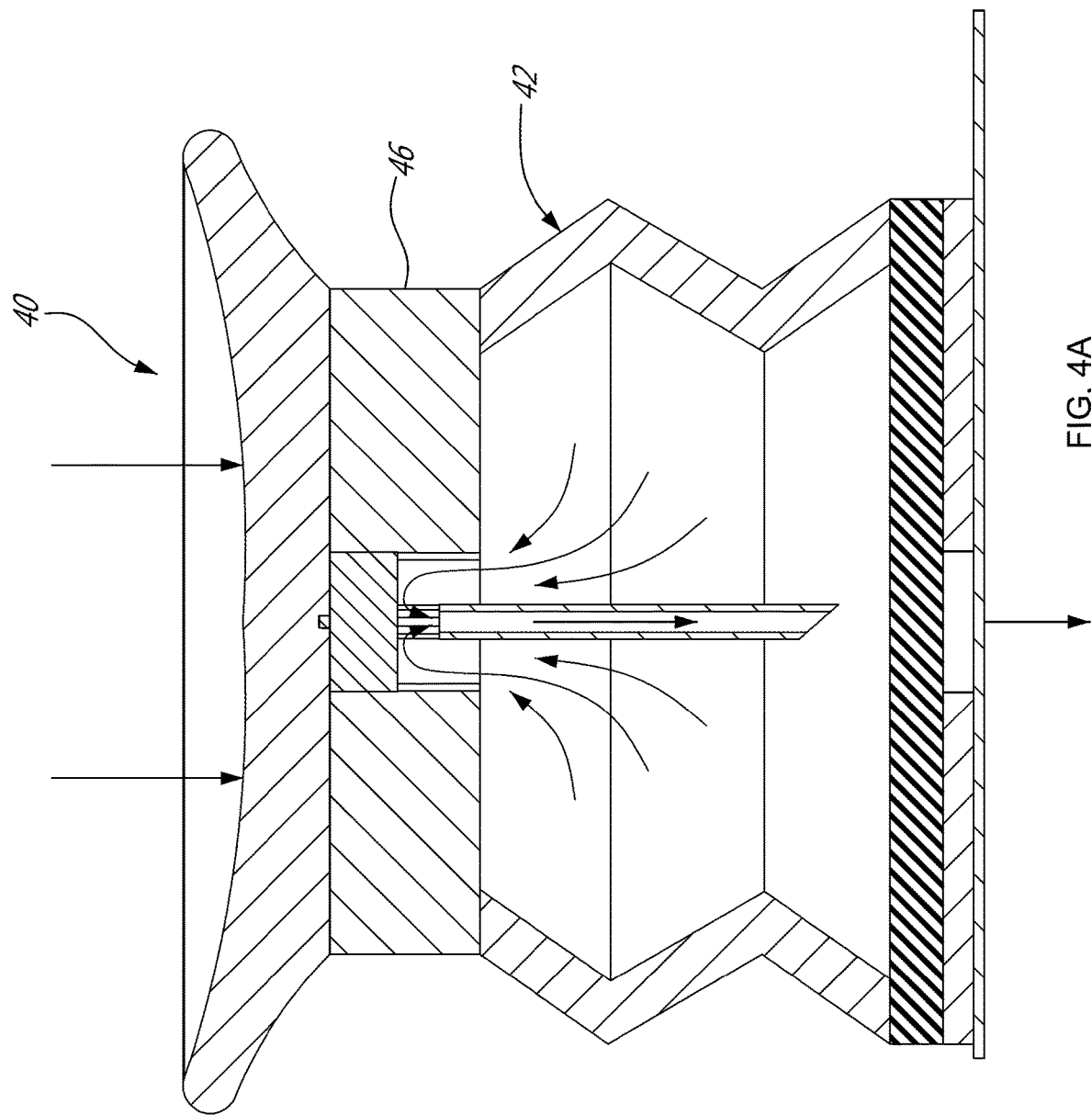
FIG. 4a schematic diagram, based on FIG. 4, showing the flow of the liquid in the injector when in operation.

As shown in FIG. 4, the end wall 45 could also be provided with an alcohol swab pad 62 adhered thereto. A peel-cover strip 64 may be added to cover the alcohol swab pad in lieu of the cap 43. Other antiseptic materials may also be provided on the end wall 45.

The injector 40 is designed for any injectable medicinal liquid requiring a dose of 1 mL. The liquid may be prepackaged vaccine. To administer the vaccine to a patient, the cap 43 is first removed and then the injector 40 is placed, with the end wall 45, against the skin of a patient. A slight pressure is then applied to the press block 48 causing the accordion walls of the barrel 44 to to expand laterally storing energy while creating a pressure on the fluid and the needle 50 to move forward piercing the septum or end wall 45 and ultimately the skin of the patient. Once the pressure is relieved from the press block 48, the accordion wall of barrel 44 will regain its original shape as a result of the stored energy accumulated when it was expanded, thus retracting the needle 50 within the barrel 44. During the movement of the of the press block 48, expanding the barrel 44, pressure was applied to the vaccine liquid in the reservoir, from the stored energy in the wall of the barrel 44, forcing the liquid through the ports 56 of the needle 50, down through the bore 60 and into the patient. FIG. 4c illustrates the flow of the vaccine liquid in the reservoir moving upstream, somewhat counter to the direction of the movement of the plunger 46, towards the port 56.

Figure 6:
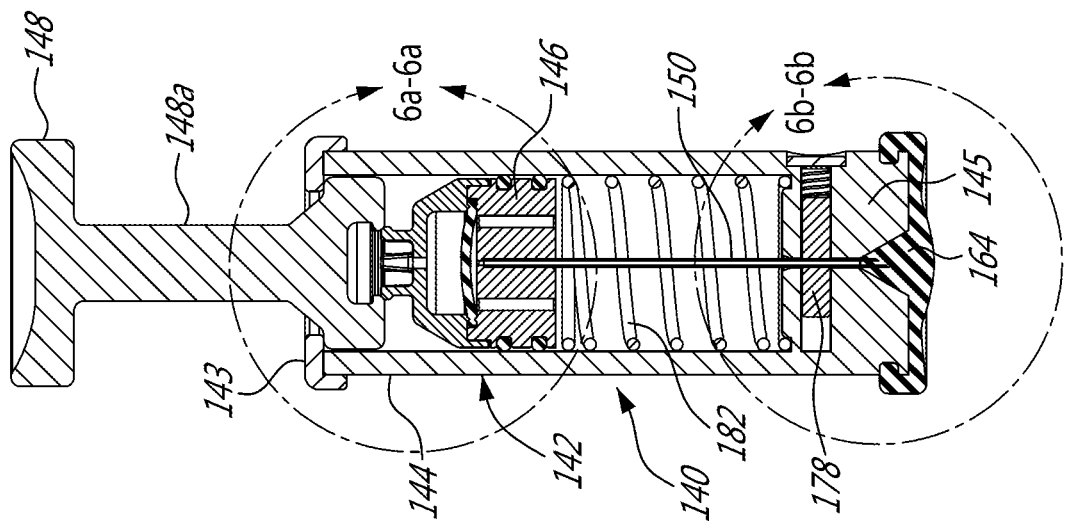
FIG. 6 is a longitudinal cross section taken through lines 6-6 of FIG. 5.
Figure 5:
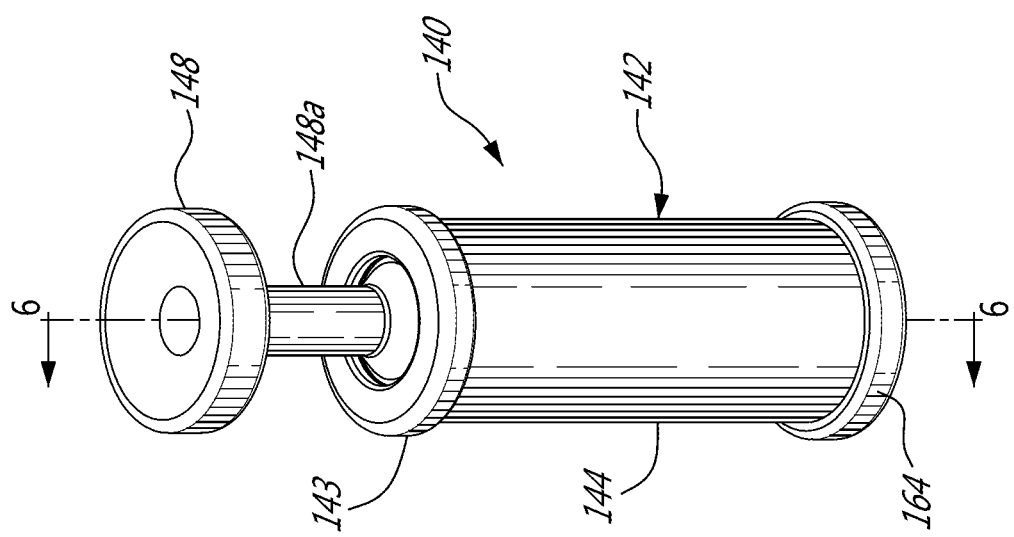
FIG. 5 is a perspective view of another embodiment of the injector.
Figure 6C:
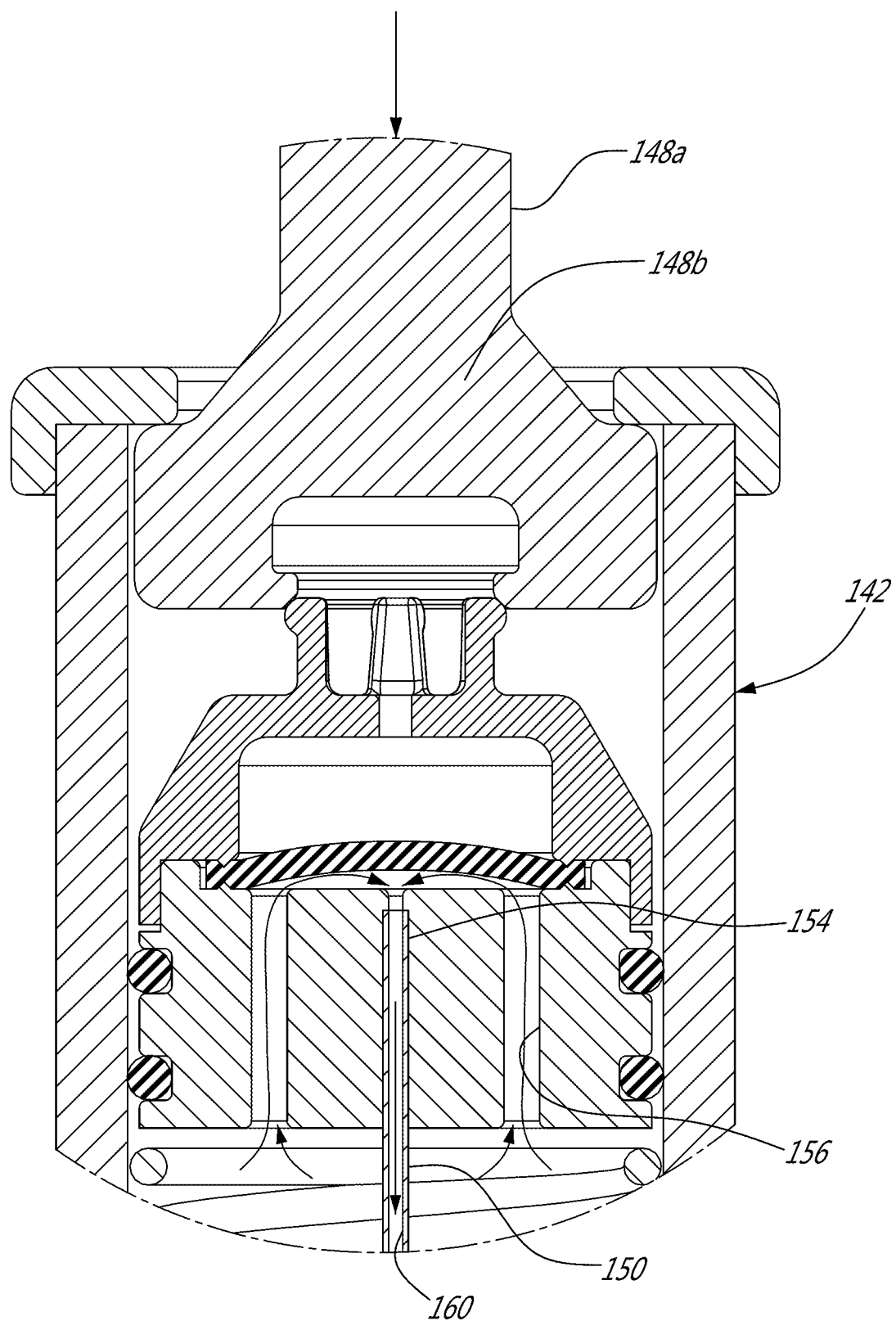
FIG. 6c is a schematic diagram based on FIG. 6a showing the flow of the liquid in the injector when in operation.

FIGS. 5 through 6c illustrate another embodiment of the injector for use as a transcutaneous injector. In this embodiment the injector 140 includes a syringe 142 with a barrel 144 having a rigid, cylindrical wall. The proximal end of the barrel 144 includes a cap 143 defining a central opening 143a. The distal end of the barrel 144 comprises an end block 145 defining a bore 162. A septum 164 fills the enlarged end of the bore 162. The septum 164 is in the form of a cap anchored to the side wall of the end block 145.

A plunger 146 is adapted to move axially within the cylindrical barrel 144 and includes pair of O-rings 147 that acts as seals between the wall of the barrel 144 and the plunger 146. The plunger 146 is provided with a cavity 168 which includes an expansion chamber 152 contained by a membrane 166. The membrane 166 may be of a silicone material adapted to expand within the cavity 168. Any similar elastomeric material may be used. A reservoir, for receiving a drug or other liquid medicine, is formed between the plunger 146 and the end block 145 in the barrel 144. Conduits defined by bores 156 traverse the plunger 146, parallel to the axis of the barrel 144. The conduits 156 communicate between the reservoir portion of the barrel 144 and the expansion chamber 152. A needle 150 is anchored to the plunger 146, at the base of the needle 154. The needle 150 extends from the plunger 146 axially through the reservoir portion and into the bore 162 of end block 145. The tip 158 of the needle sits within the septum 164. The needle 150, by means of its bore 160, communicates with the expansion chamber 152. The plunger 146 moving within the rigid wall of barrel 144 ensures that the needle 150 will be centered.

A press handle 148 includes a head, a stem 148a and an enlarged base 148b. The proximal end of the barrel 144 receives the enlarged base 148. A cavity 172 is defined in the base 148b and includes a collar 174 defining the mouth of the cavity 172. The proximal end of the plunger 146 comprises a cap 149 which includes a venting bore 170 surrounded by spaced apart axially extending fingers 171. Each finger 171 has a laterally enlarged tip, adapted to engage the collar 174 when pressure is applied in an axial direction by the press handle 148.

A coil spring 182 extends between the plunger 146 and the end block 145, within the barrel 144.

The end block 145 defines a transverse bore 176 intersecting the bore 162. A shuttle 178 is adapted to slide within the bore 176 and includes a transverse bore 178a through which the needle 150 extends in its default position. A spring 180 is held in the bore by cap 182, compressed against the shuttle 178.

In operation, when it is required to inject a drug or other medicinal fluid transcutaneously into the body of a patient, the septum portion 164 of the injector 140 is pressed against the skin of the patient. Pressure is then applied to the press handle 148 forcing the plunger 146 to slide within the barrel 144 towards the end block 145 thus advancing the needle 150. The liquid within the reservoir will move through the conduits 156 into the expansion chamber 152 expanding the membrane 166 and thus forcing the liquid to enter the bore 160 of needle 150. With a short travel, the tip 158 of needle 150 will pierce the septum 164 and the skin of the patient delivering the liquid into the patient's body. As the plunger 146 comes to the end of its travel against the compressed spring 182, and pressure continues to be applied to the press handle 148, the fingers 171, at the proximal end 149 of the plunger 146, will snap into the cavity 172 and be trapped by the collar 174. The snapping sound will alert the person administrating the injection that the dose has been completed. Furthermore, the overall length of the press handle 148, the plunger 144 and the needle 150 has now been reduced, as will be explained in greater detail.

Once pressure is relieved from the press handle 148, the compressed coil spring 182 will cause the plunger 146 to retract the needle 150 back into the barrel 144. Once the needle tip 158 clears the shuttle 178 the spring 180 will cause the shuttle to move laterally within the bore 176 thus blocking the path of the needle 150 from further use. The needle 150 will have traveled far enough, while being retracted, to clear the tip 158 from the bore 176 due to the fact that length of the combined press handle 148, plunger 144 and the needle is shorter.

For a better understanding of the operation, it is noted, as shown in FIG. 6c, that the flow of the liquid moves counter to the direction of the plunger 146 from the reservoir in the barrel through the conduits 156 to the expansion chamber 152 and ultimately the the open proximal end of the needle 150. The purpose of such an arrangement, that having the reservoir of liquid in the chamber with the needle is to reduce the size of the injector. Most prior art injectors have the needle, reservoir and plunger in series alignment, thereby preventing a design that is as compact as possible.

It should be noted that the following embodiments are conceptual and the illustrations are schematic. The dimensional proportions may not always the accurate but are merely suggestive to the person skilled in the art. As with the embodiments illustrated in FIGS. 1 to 6b, the injectors are meant to include small doses of approximately 1 mL. Thus the overall dimensions of the syringes will be in the order of 1 or 2 cm.

Figure 8:
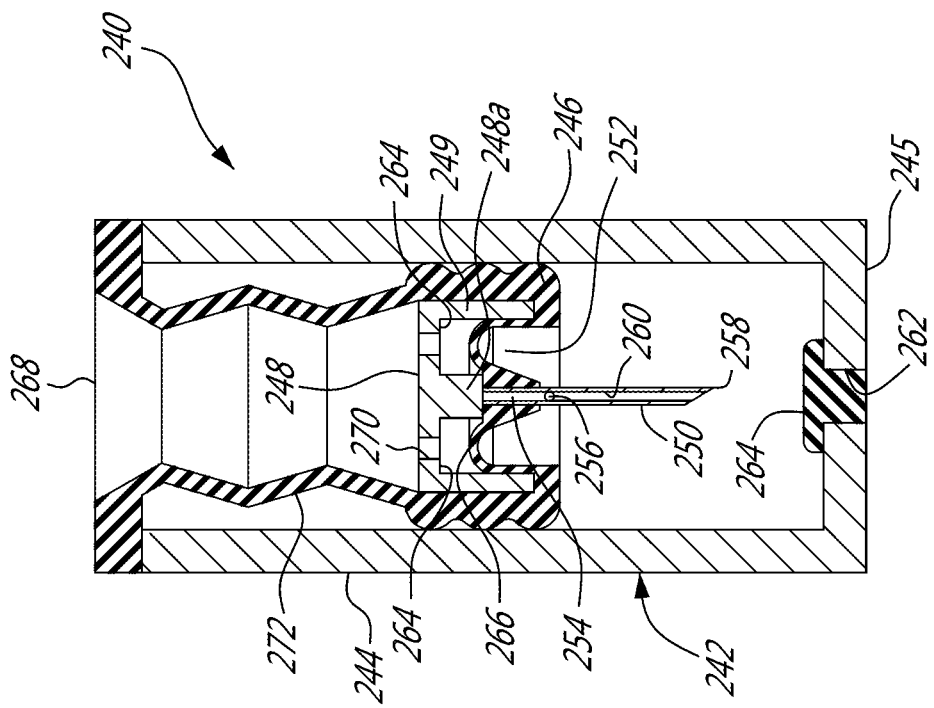
FIG. 8 is a longitudinal cross section taken through lines 8-8 of FIG. 7.
Figure 7:
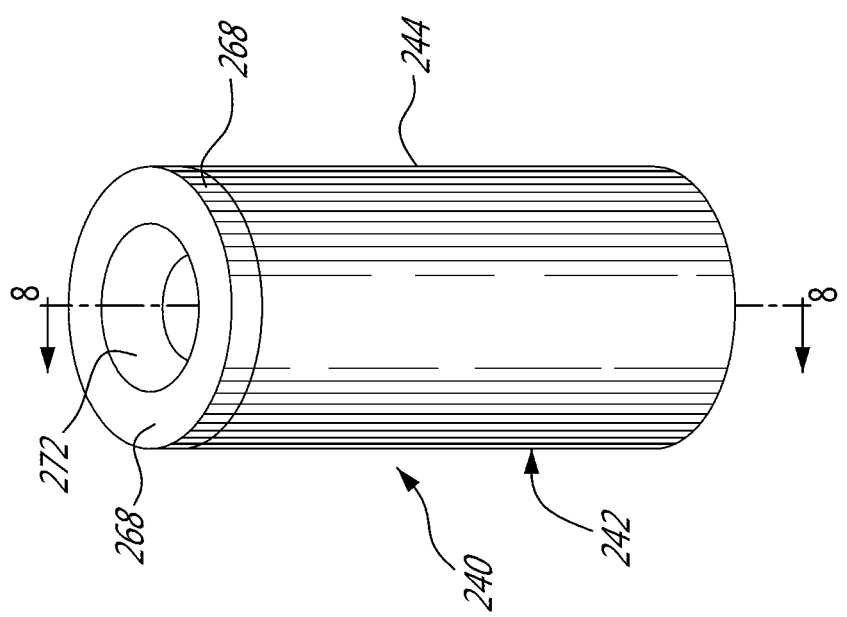
FIG. 7 is a perspective view of yet another embodiment of the injector.

In the embodiment shown in FIGS. 7 and 8, the injector 240 includes a syringe 242 with a rigid cylindrical barrel 244. The barrel 244 includes an end wall 245 defining a central opening 262 in which a septum 264 is located. A plunger 246 slides within the barrel 244 defining a reservoir between the end wall 245 and the distal end of the plunger 246.

The plunger 246 includes, at its proximal end an accordion shaped sleeve 272 ending in a collar 266 fitted at the distal end of the barrel 244. The plunger including the proximal sleeve 272 and collar 268 may be of an elastomeric material acting as an energy storage device as will be described further. A press plate 248 is contained within the sleeve 272. The press plate 248 has a cylindrical skirt 249 and a central axial projection 248a defining an annular cavity 264. The rigid press plate 248, with its skirt 249, adds structure to the plunger 246. The needle 250 is anchored to the central projection 248a, at its base 254. A membrane 266 is located within the annular cavity 264 and forms a expansion chamber 252 within the plunger 246. Vent openings 270 are defined in the press plate 248. The needle 250 includes ports 256 within the confines of the expansion chamber 252 for communicating the drug from the reservoir to the bore 260 of needle 250.

In operation, when it is required to inject a vaccine or drug into a patient, the end wall 245 of the syringe 242 is applied to the skin of the patient and pressure is applied to the press plate 248 thus advancing the needle 250 through the septum 264 and the skin of the patient. As the plunger 246 advances, the sleeve 272 will be stretched and the liquid drug within the reservoir will expand the membrane 266 within the annular cavity 264. The pressure applied by the membrane 266 on the liquid forces the drug through the ports 256, the bore 260 of the needle 250 and into the patient.

Figure 10:
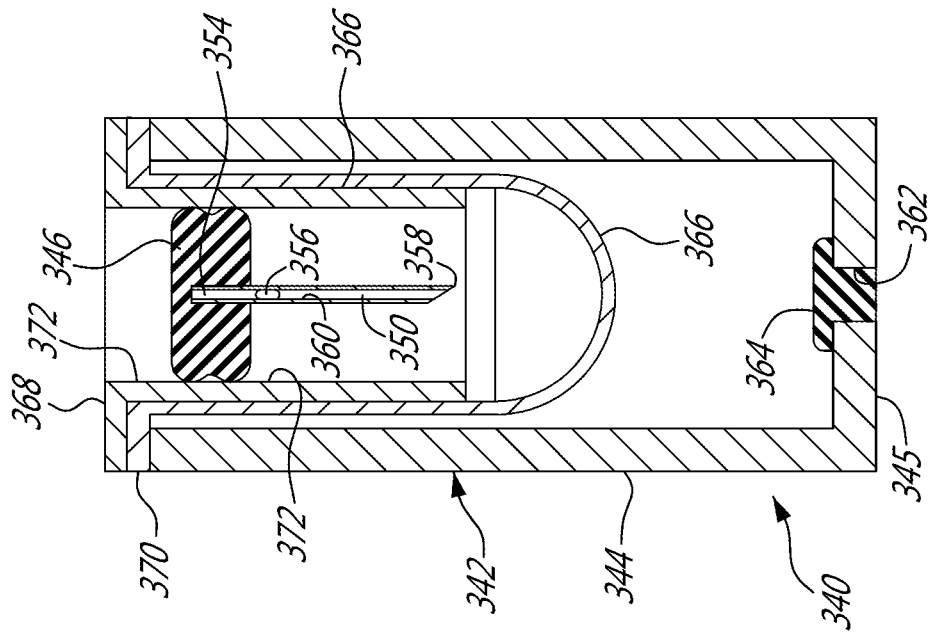
FIG. 10 is a longitudinal cross section taken through lines 10-10 of FIG. 9.
Figure 9:
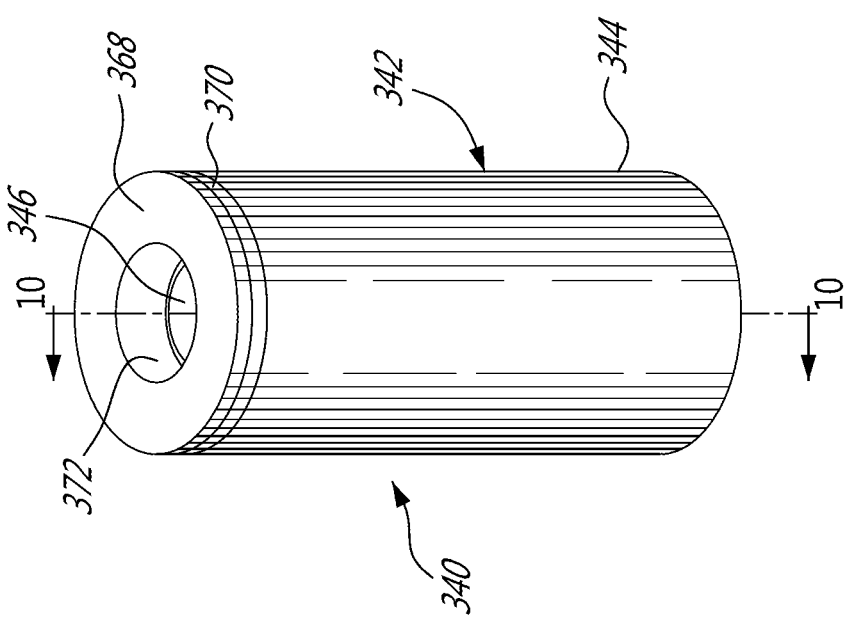
FIG. 9 is a perspective view of still another embodiment of the injector.

FIGS. 9 and 10 show yet another embodiment of the injector 340 with a syringe 342 including a barrel 344 made up of a rigid cylindrical tubular wall and an end wall 345. A pouch-like membrane 366 including a collar 370 extends within the barrel 344 from the proximal open-end of the barrel 344. A rigid sleeve 372 having a collar 368 retains the membrane collar 370 against the rim of the barrel 344 at the proximal end thereof. A plunger 346 slides within the sleeve 372 in sealing contact with the inner surface thereof. The plunger 346 also serves as the press plate. The drug is stored within the reservoir defined by the membrane 366, the plunger 346 and the sleeve 372. A needle 350 is anchored in the plunger 346 at its base 354. Ports 356 are provided in the needle 350 in communication with the liquid drug within the reservoir and a hollow bore 360 of the needle 350. The needle 350 has a sharp tip 358.

In operation, as pressure is applied to the end plate/plunger 346, the needle 350 will advance, piercing the membrane 366 against the end wall 345, allowing the tip of the needle 358 to pass through the septum 364 in opening 362 and through the skin of the patient. The liquid drug will, under pressure of the extended membrane 366 pass through the ports 356 and the bore 360 of needle 350.

Figure 12:
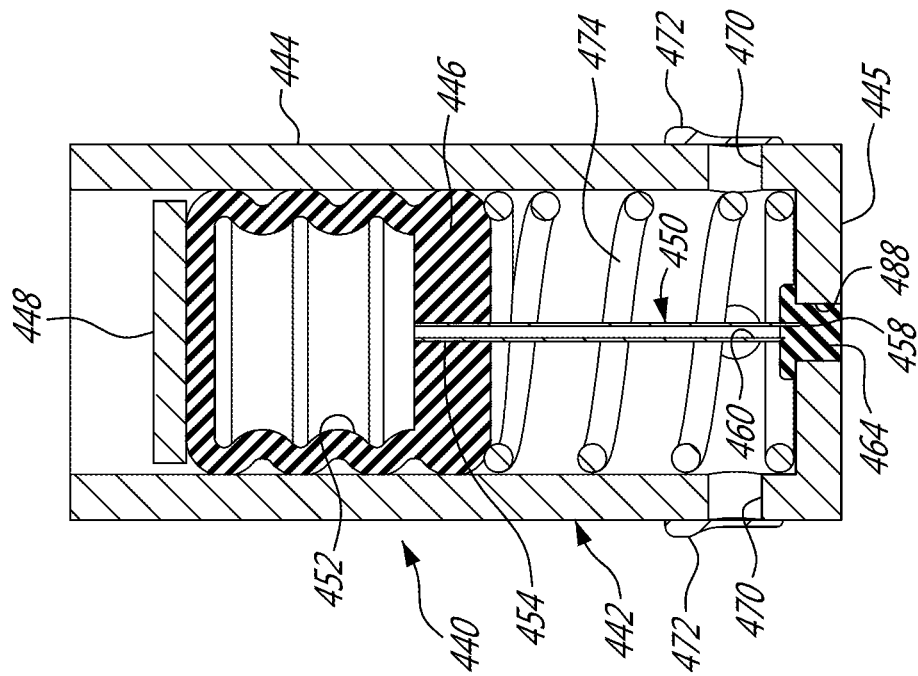
FIG. 12 is a longitudinal cross section taken through lines 12-12 of FIG. 11.
Figure 11:
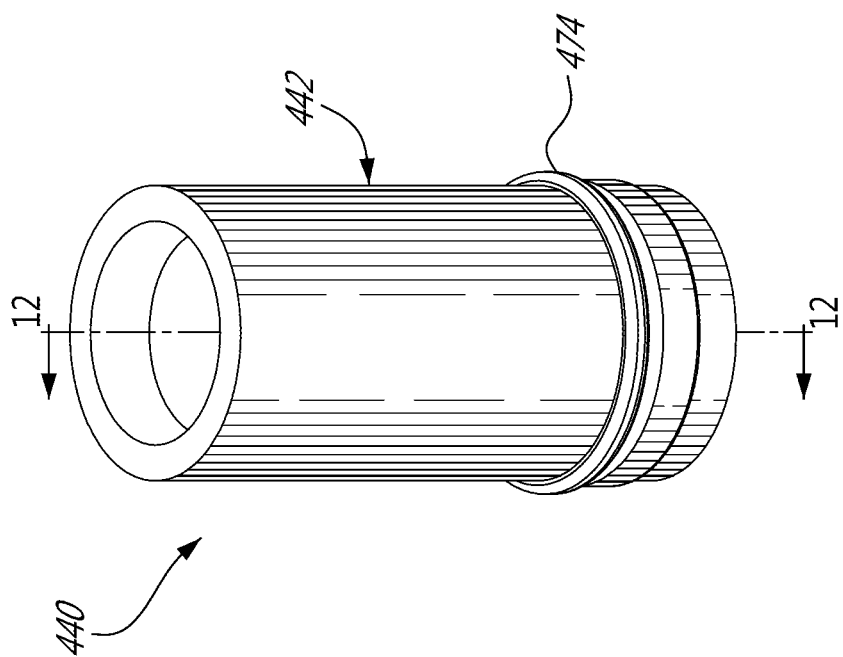
FIG. 11 is a perspective view of a further embodiment of the injector.

FIGS. 11 and 12 show another embodiment of an injector 440, suitable for injecting, transcutaneously, a vaccine, or other medicinal fluids. The injector 440 includes a syringe 442 having a rigid cylindrical barrel 444 with an end wall 445. The end wall includes an opening 462 in which is provided a septum 464. A plunger 446 slides within the barrel 444 but is retained in a default position, as shown, by means of a coil spring 474. The plunger 446 defines a closed cavity representing a reservoir 452 for the medicinal liquid or vaccine. The plunger 446 is in the form of an accordion made up of an elastomeric material. An end plate 448 is provided at the proximal end of the plunger 446. A needle 450 is anchored at its base 454 to the distal end of the plunger 446. The hollow bore 460 of the needle 450 communicates with the reservoir 452. The space formed between the plunger 446 and the end wall 445 includes the coil spring 474. Vents 470 are provided to permit displacement of the air within the space of the barrel 444. A sliding sleeve 472 is provided to block or open the vents 470.

In operation, the syringe 442 is placed with the end plate 445 against the skin of the patient and pressure is applied to the press plate 448 thereby advancing the needle 450 through the septum 464 and through the skin of the patient. Further pressure on the press plate 448 causes the accordion wall of the proximal portion of the plunger 446 to collapse, forcing the drug within the reservoir 452 to pass through the bore 460 of needle 450 into the patient. Once pressure is released from the press plate 448 the coil spring 474 will retract the plunger 446 to its default position, withdrawing the needle 450 into the confines of the barrel 444.

Figure 14:
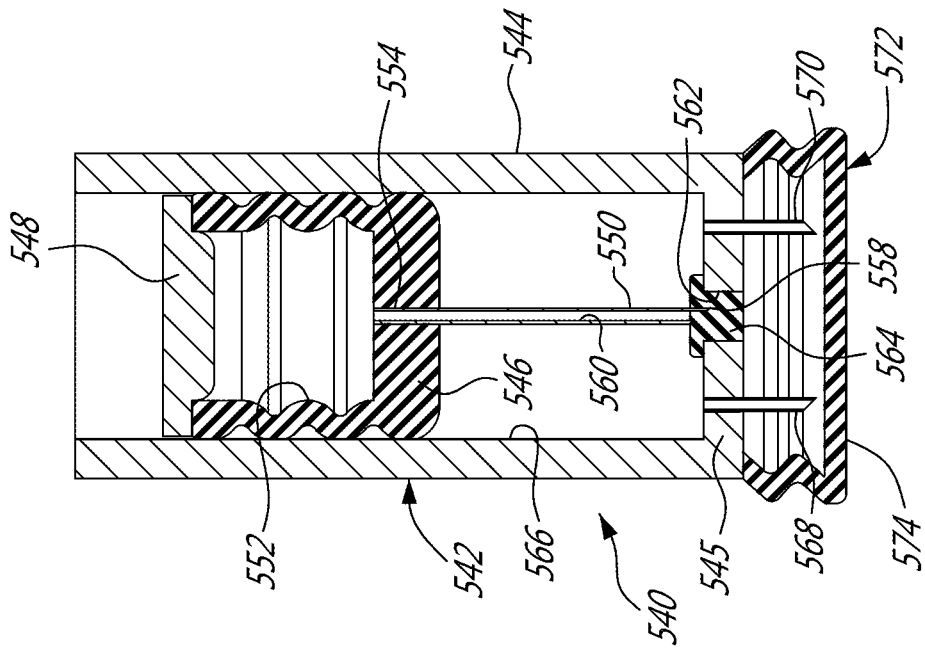
FIG. 14 is a longitudinal cross section taken through lines 14-14 of FIG. 13.
Figure 13:
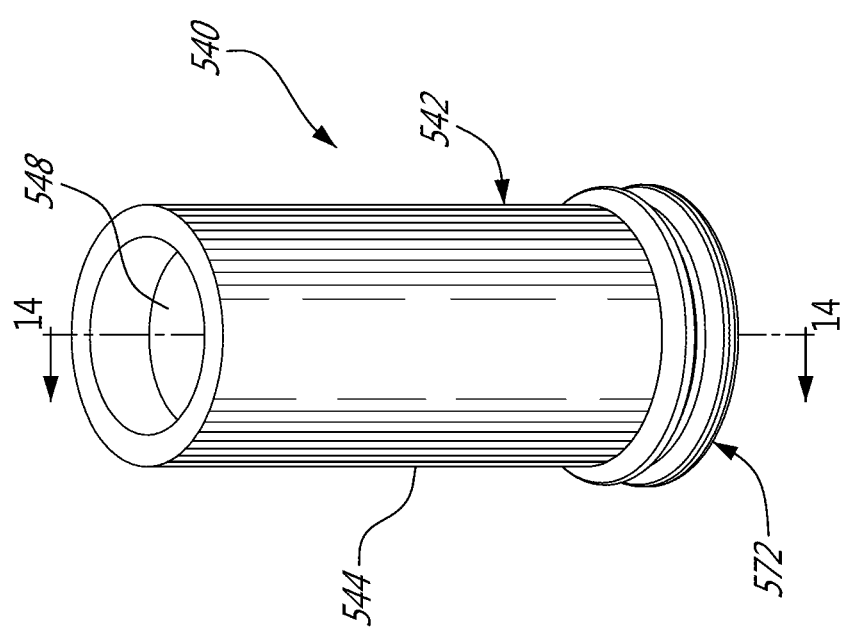
FIG. 13 is a perspective view of yet a further embodiment of the injector.

The embodiment shown in FIGS. 13 and 14 illustrate an injector which can simultaneously inject separate doses of two different drugs. The injector 540 includes a rigid cylindrical barrel 544 making up part of syringe 542. The barrel 544 includes a rigid end wall 545 with its central opening 562 and a septum 564. An energy storing, bellows-type barrel 572 extends, beyond end wall 545, in the axis of the barrel 544 and includes an end wall 574. The bellows-type barrel 572 defines a chamber into which secondary needles 568 and 570 extend from the end wall 545. The needles 568 and 570 communicate with a reservoir 566 defined in the barrel 544, between the plunger 546 and the end wall 545. The plunger 546 is of the type defined in FIG. 12 which contains a cavity defining a first reservoir 552. A press plate 548 seals the reservoir 552. A needle 550 extends from the distal end of the plunger 546 and is anchored thereto at its base 554. The distal end 558 of the needle 550 sits in the septum 564. The hollow bore 560 of needle 550 communicates with the first reservoir 552 containing a first drug. The second reservoir 566 contains the second drug communicating with the secondary needles 568 and 570. FIG. 14 will also include a coil spring, such as in FIG. 12, to return the plunger 546.

In operation, when it is required to inject the two drugs independently into the patient, the end wall 574 of the bellows-type barrel 572 is put in contact with the skin of the patient and pressure is applied against the syringe 542 to collapse the bellows type barrel 572 and allow the needles 568 and 570 to penetrate the skin of the patient. Pressure is also applied to the press plate 548 forcing the plunger 546 to move the drug in reservoir 566 through the needles 568 and 570 while needle 550 advances through the septum and eventually through the end wall 574 into the patient to inject the drug from reservoir 552, under the pressure applied to the press plate 548. A coil spring as shown in FIG. 12 may be included in the present embodiment to retract the plunger 546. However, upon releasing pressure on the syringe and the press plate, the bellows-type barrel 572 will retract the needles 568 and 570; and the coil spring will retract the plunger 546 and the needle 550.

Figure 16:
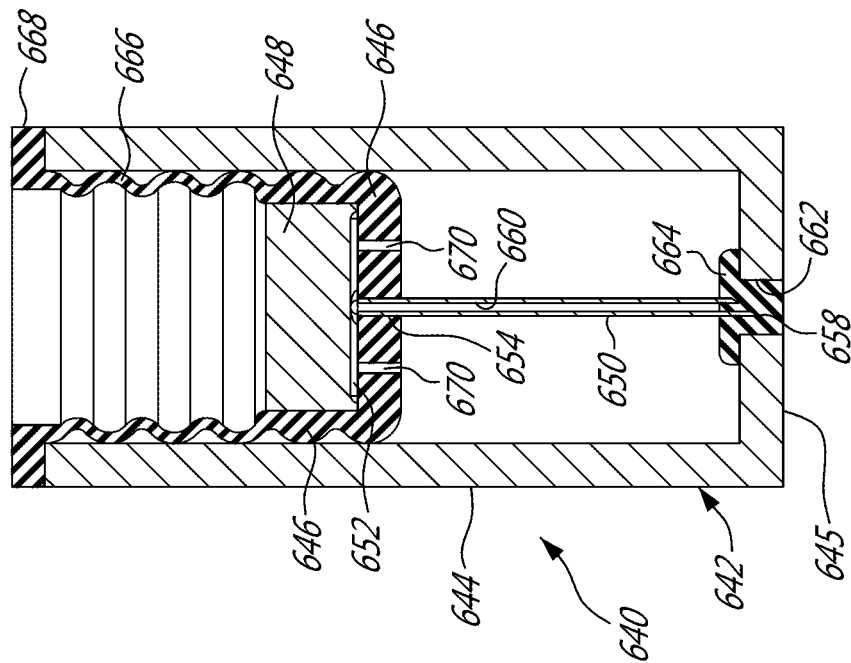
FIG. 16 is a longitudinal cross section taken through lines 16-16 of FIG. 15.
Figure 15:
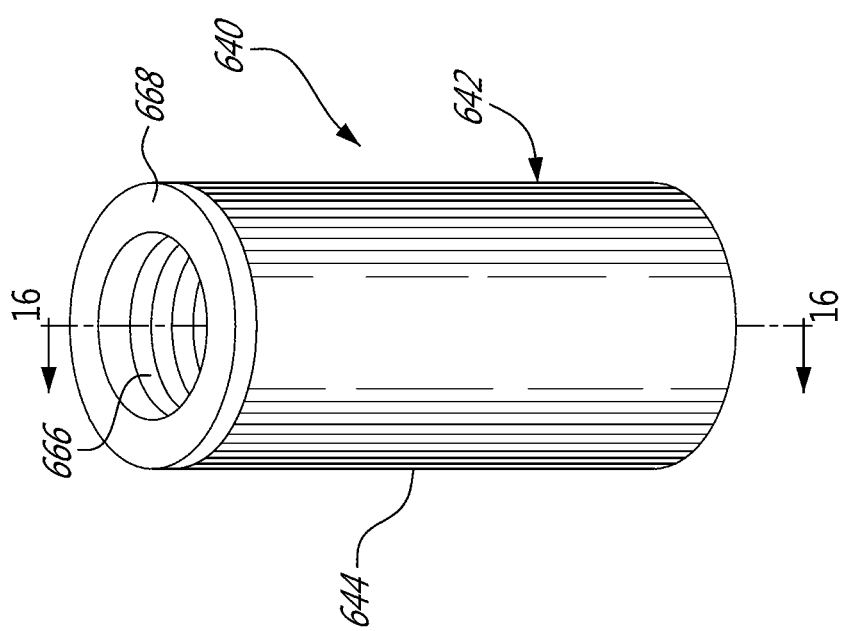
FIG. 15 is a perspective view of a still further embodiment of the injector.

FIGS. 15 and 16 show another embodiment where the injector 640 includes a syringe 642 with a rigid cylindrical tube forming the barrel 644. A plunger 646 includes an energy storing sleeve 666 terminating in a collar 668 at the proximal end of the barrel 644. The barrel 644 includes an end wall 645 at the distal end thereof with an opening 662 and the septum 664 stuffed within the opening 662. A needle 650 is anchored at its base 654 to the plunger 646. The needle 650 includes a bore 660 and a sharp tip 658. The tip 658 is embedded in the septum 664.

A press block 648 is provided within the sleeve 666 forming part the plunger 646 and defines a expansion chamber 652 between the press block 648 and the plunger 646. The end wall of the plunger 646 is likewise elastic, made from the same material as the sleeve 666 thereby creating a an expansion chamber 652. Bores 670 extend through the end wall of the plunger 646 in communication with the expansion chamber 652. The liquid medication would be stored in the reservoir formed by the barrel 644 between the plunger 646 and the end wall 645.

In operation, the syringe 642 is pressed up against the patient's skin with the wall 645 in contact therewith. As pressure is applied to the press block 648 the plunger 646 will move towards the end wall 645 advancing the needle 650 such that the tip 658 penetrates the skin of the patient. The medication in the reservoir will be forced to flow through the bores 670 into the expansion chamber 652 and then down through the bore 660 of the needle 650. Once the pressure is released from the press block 648, the sleeve 666 will retract the plunger 646 as well as the needle 650, returning the needle 650 into the barrel 644.

Figure 18:
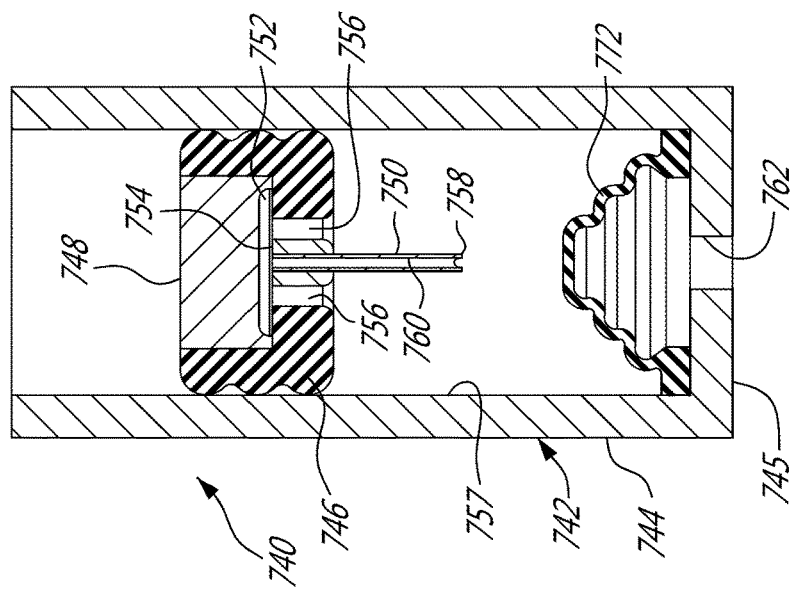
FIG. 18 is a longitudinal cross section taken through lines 18-18 of FIG. 17.
Figure 17:
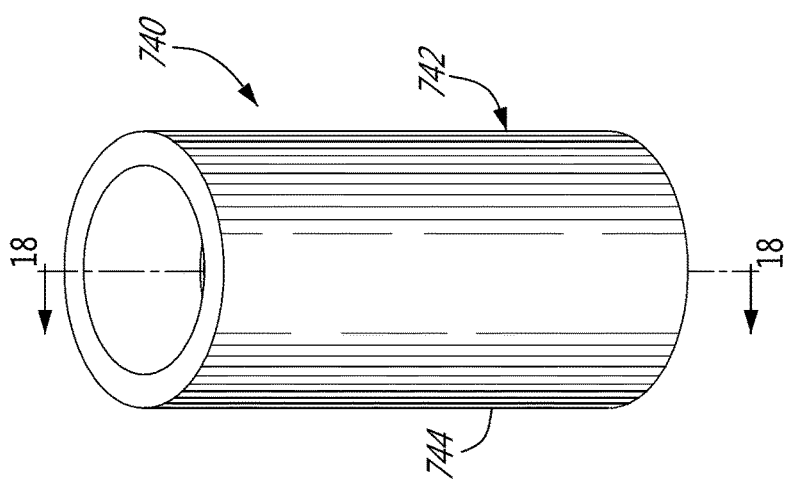
FIG. 17 is a perspective view of an alternative embodiment of the injector.

The injector 740 shown in FIGS. 17 and 18 includes a rigid cylindrical tubular barrel 744 forming the syringe 742. The barrel 744 also includes an end wall 745 with a central opening 762. An elastomeric plunger 746 is provided for sliding movement within the barrel 744. The plunger 746 houses a press block 748 defining a expansion chamber 752 within the plunger 746. Bores 756 communicate the expansion chamber 752 with a reservoir 757, containing the drug in liquid form, within the barrel 744. A needle 750 is anchored in the plunger 746 at its base 754. The needle includes a bore 760 and a tip 758. A cone-shaped bellows 772 is sealed against the end wall 745 and defines the reservoir 757 with the plunger 746 and the wall of the barrel 744.

In operation, the syringe 742 is pressed against the patient's skin by contact with the end wall 745. As the pressure is applied to the press block 748, the plunger 746 moves axially within the barrel 744 where the bellows 772 applies pressure to the liquid within the reservoir 757 forcing the liquid to pass through bores 756 into the expansion chamber 752 and the needle 750, as the needle tip 758 pierces the skin of the patient. The bellows 772 is also pierced by the needle 750 during its travel.

Figure 19:
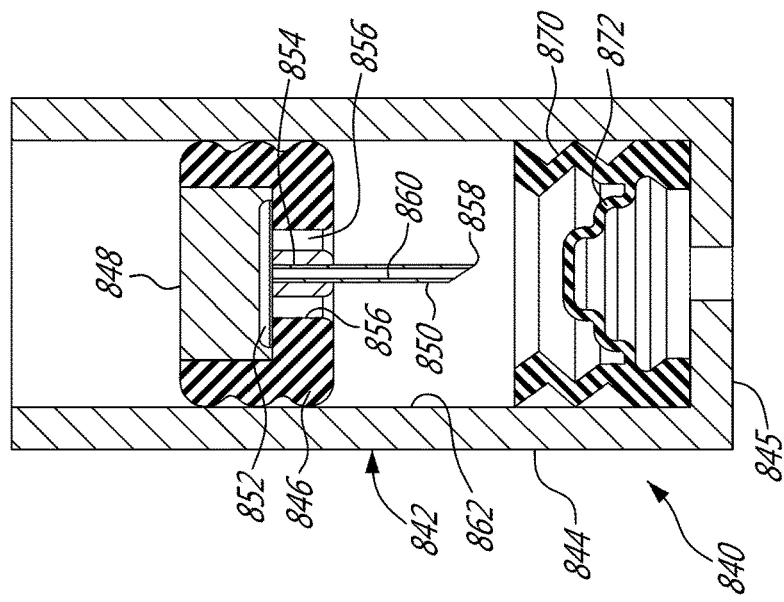
FIG. 19 is a longitudinal cross section similar to FIG. 18 but showing a structural modification thereto.

The embodiment in FIG. 19 is similar to that shown in FIGS. 17 and 18 but the numerals, identifying the parts, have been raised by 100. An additional accordion sleeve 870 is integrated with the energy storing bellows 872. The material of sleeve 870 is the same as that of the bellows 872 that is it is an elastomeric material capable of storing energy. Thus, when pressure is released from the press block 848 after the injection of the drug into the patient's body, the accordion sleeve 870 will effectively return the plunger 846 and therefore the needle 850 to a default position with the needle 850 completely retracted into the barrel 844.

Figure 21:
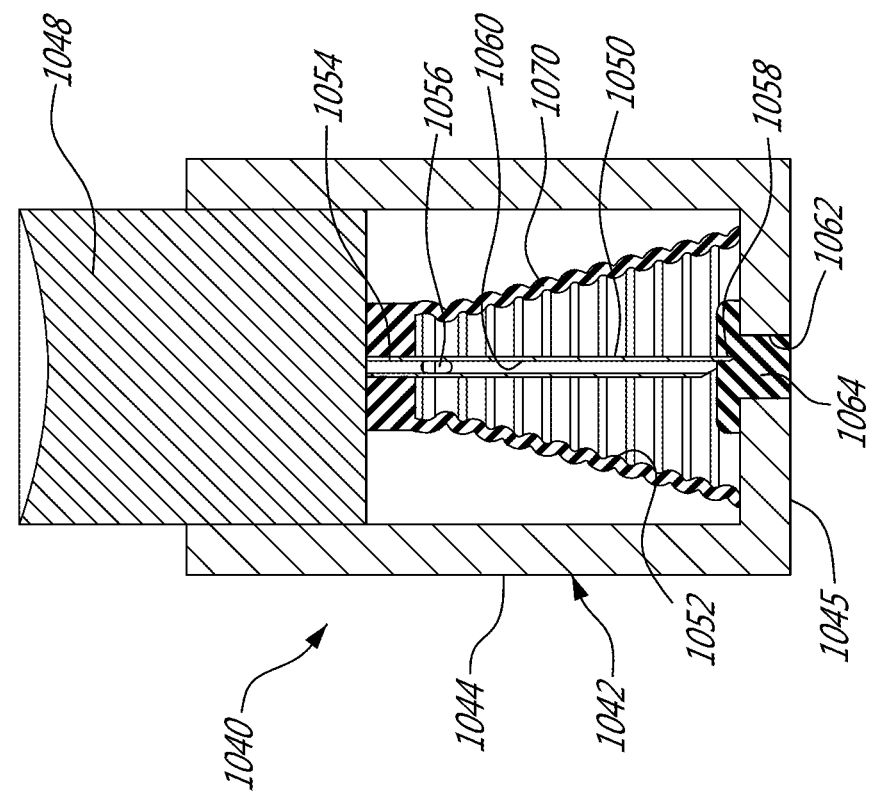
FIG. 21 is a longitudinal cross section taken through lines 21-21 of FIG. 20.
Figure 20:
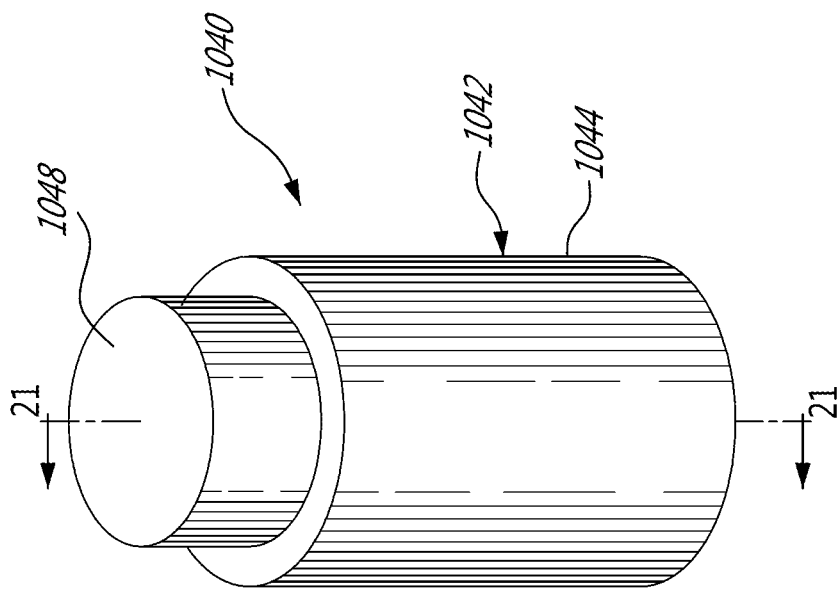
FIG. 20 is a perspective view of a further alternative embodiment of the injector.

Referring now to the embodiment shown in FIGS. 20 and 21 there is provided an injector 1040 that includes a syringe 1042 with a rigid cylindrical barrel 1044. The plunger is in the form of a press block 1048 inserted at the proximal end of the barrel 1044. The barrel includes an end wall 1045 defining a central opening 1062 in which a septum 1064 is fitted. A needle 1050 is anchored to the plunger/press block 1048 at its base 1054. The needle has a bore 1060 and ports 1056 at its proximal end and a sharpened tip 1058 at its distal end.

A conical shaped hollow bellows 1070 is provided within the barrel 1044. The bellows 1070 has its base sealed to the end wall 1045 and its apex sealed about the base 1054 of the needle 1050 and the distal surface of the plunger/press block 1048. The liquid drug is maintained within a reservoir 1052 contained within the bellows 1070.

In operation, as pressure is applied to the press block 1048, when the end wall 1045 engages the skin of a body, the bellows 1070 compresses, forcing the drug within the reservoir 1052 to pass through the ports 1056 and the needle 1050. The needle tip 1058 pierces the skin of the patient and of the drug flows into the patient from the needle 1050. Once pressure is released from the press block 1048, the bellows 1070 will retract the press block 1048, as well as the needle 1052, to their default position within the barrel 1044.

Figure 23:
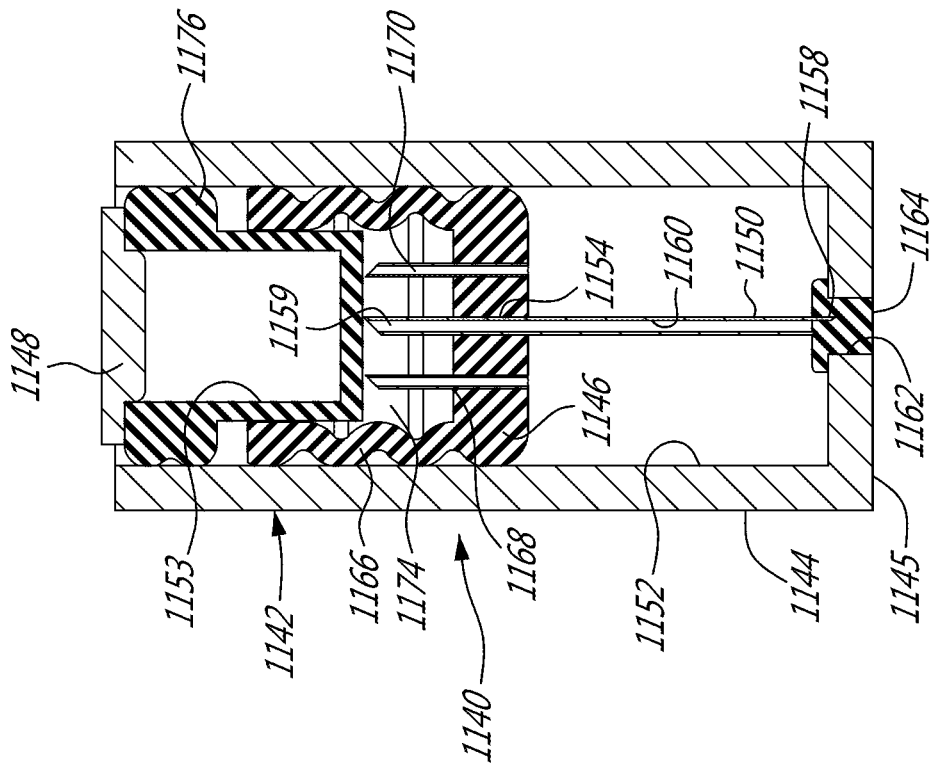
FIG. 23 is a longitudinal cross section taken through lines 23-23 of FIG. 22.
Figure 22:
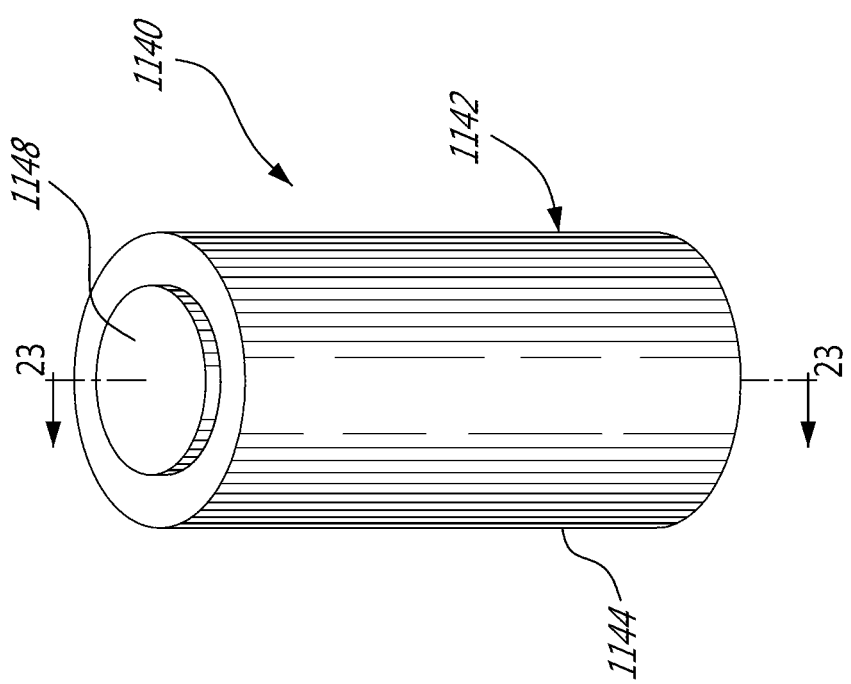
FIG. 22 is a perspective view of a still further alternative embodiment of the injector.

The next embodiment shown in FIGS. 22 and 23 contemplates a drug that is to be mixed on-site. That is two components making up a solution, are mixed. One component might be a powder and the other a liquid that are mixed as the injection is being administered.

An injector 1140 includes a syringe 1142 with a rigid cylindrical barrel 1144 and a distal end wall 1145. An opening 1162 is defined in the end wall 1145 and is filled with a septum 1164. A plunger 1146 includes an elastomeric sleeve 1166 which defines a cavity 1174. A second plunger 1176 is inserted at the proximal end of the sleeve 1166 and defines a second reservoir 1153. A first reservoir 1152 is defined between the plunger 1146 and the end wall 1145. A needle 1150 is anchored in the plunger 1146 at its base 1154 and includes a proximal extension 1159 with a sharpened tip. The needle 1150 includes an axial bore 1160 and a sharpened tip 1158 which is embedded in the septum 1164. Secondary needles 1168 and 1170 are also provided in the plunger 1146 and extend towards the secondary plunger 1176 with sharpened tips. The needles 1168 and 1170 are in communication with the reservoir 1152. Finally a press plate 1148 seals the reservoir 1153 at the proximal end of the second plunger 1176.

A liquid may be provided in the reservoir 1152 and a powder such as a salt may be provided in the second reservoir 1153.

In operation, as the syringe 1142 is pressed against the patient's skin, pressure is applied to the press plate 1148 causing the second plunger 1176 to move axially within the sleeve 1166 causing the needles 1168, 1170 and 1159 to pierce the thin wall of the second plunger 1176. Further pressure on the press plate 1148 forces the plunger 1146 to move axially towards the end wall 1145 thus allowing the needle 1152 pierce the skin of the patient. The movement of the plunger pressurizes the reservoir 1152 causing the liquid solution to pass through needles 1168 and 1170 into the second reservoir 1153 where it is mixed with the other component such as the salts to form the solution. The mixed solution then passes through the needle 1150 into the body of the patient.

This embodiment may be useful where a soluble powder such as a salt, which is added to make the drug reactive, cannot be mixed prior to injection because of chemical instability of the mixture.

The following examples are alternatives to the needle-blocking device described in FIGS. 6 and 6b. Only that portion of the syringe will be illustrated in the following embodiments.

The embodiment shown in FIGS. 24 to 25a shows a syringe 1342 with a rigid cylindrical barrel 1344, end wall 1345 and an opening 1362 in the end wall, off-centre of the axis of barrel 1344. A cylindrical, rigid cap 1374 fits over the barrel 1344 at the distal end thereof and includes a spring 1372 in the space formed between the cap 1374 and the end wall 1345. An opening 1376 is defined in the end wall of the cap 1374 and is aligned with the opening 1362 in the end wall 1345, while in the default position. On the outer surface of the barrel 1344, there is a bayonet cam track 1378 cut-out in the wall. A cam follower 1380 is provided on the inner surface of the sleeve of the cap 1374 and engages the cam track 1378. The cam track 1378 has an axial component 1378a and a sloped component 1378b at an acute angle to the axial component 1378a.

In operation, when pressure is applied to move the needle 1350, the cam follower 1380 is in the position shown in FIGS. 25 and 25a, at the distal end of the cam track component 1378a. The needle 1350 passes through the septum 1364 in the opening 1362 as well as the aligned opening 1376 into the patient. Meanwhile the cap 1374 has slid axially on the barrel 1344 compressing the spring 1372. At the same time the cam follower 1380 has moved up the vertical component 1378a. When pressure is released, the needle 1350 is retracted into the barrel 1344 and the cap 1374, under the influence of the spring 1372, is returned to its extended, default position. In so doing a switch 1381, at the top of the axial component 1378a, causes the cam follower 1380 to move into the sloped component 1378b of the cam track 1378, forcing the cap 1374 to rotate 90° thus moving the opening 1376 eccentrically and out of alignment with the opening 362. Thus, the needle 1350 can no longer exit the syringe 1342.

Figure 27:
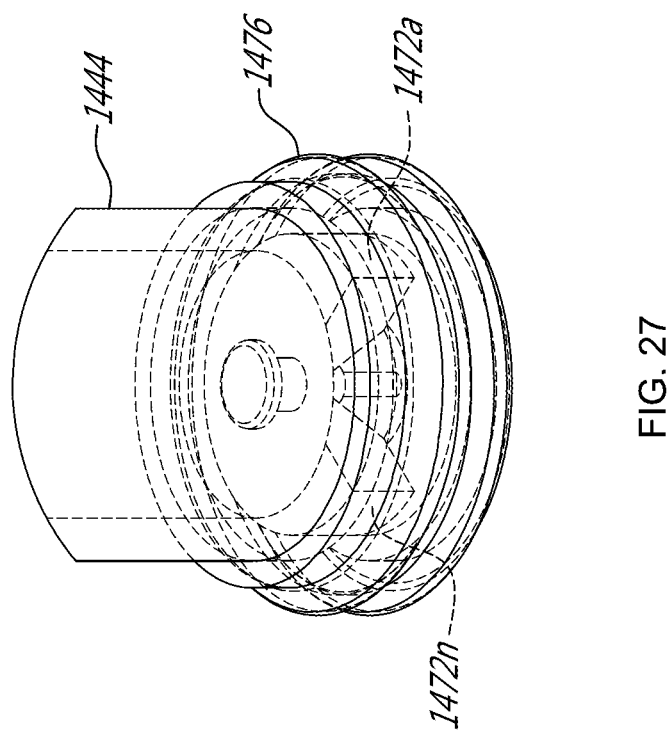
FIG. 27 is a fragmentary, perspective view showing the embodiment of FIG. 26.
Figure 26:
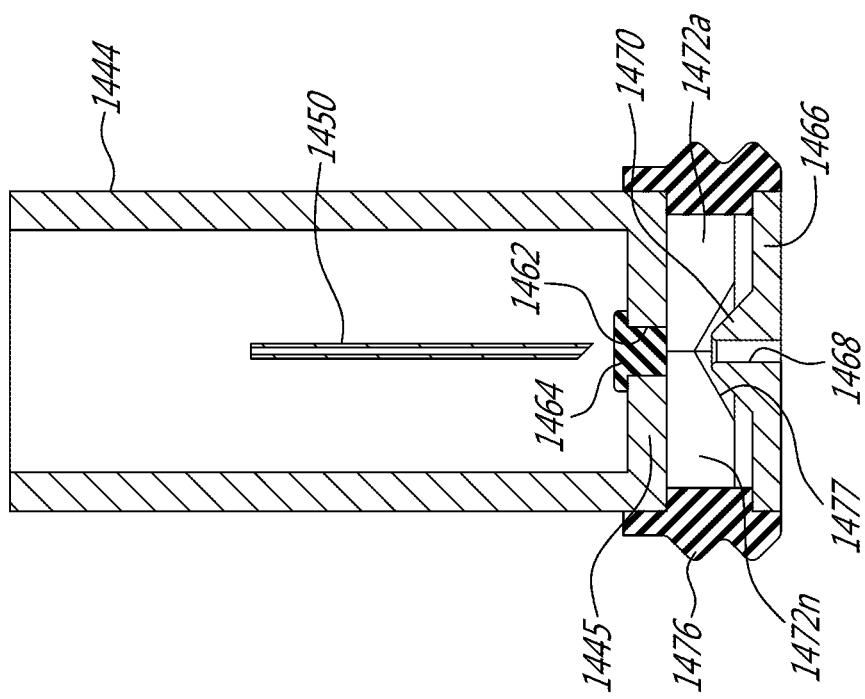
FIG. 26 is a longitudinal cross section taken though part of an injector showing another embodiment of the detail thereof.

FIGS. 26 and 27 show another embodiment of this needle deactivation detail. A syringe includes a barrel 1444 with needle 1450 aligned axially to an opening 1462 in the end wall 1445 of the barrel 1444. An elastomeric bladder 1476 extends from the barrel 1444 beyond end wall 1445. An end plate 1466, parallel to end wall 1445 defines a cavity with the bladder 1476. The end plate 1466 has a frusto-conical, axial projection 1470, with a bore 1468 passing axially therethrough. A plurality of pie-shaped blocks 1472a-1472n is located in the cavity. Each block is identical and has a beveled surface 1477 corresponding to the frusto-conical projection 1470.

In operation, as pressure is applied on the barrel 1444, the end plate 1466 will press against the patient's skin causing the bladder 1476 to expand. The frusto-conical projection 1470 will move towards the end plate 1445 forcing the blocks 1472a-1472n to move radially outwardly against the bladder 1476 thus providing a central opening aligned with the bore 1468 and opening 1462. Simultaneously, the needle 1450 will pass through the aligned openings. Once pressure is released the needle 1450 will retract within the barrel 1444 and the bladder 1476 will cause the blocks 1472a-1472n to return to their default position blocking the passage of the needle 1450.

Figure 29:
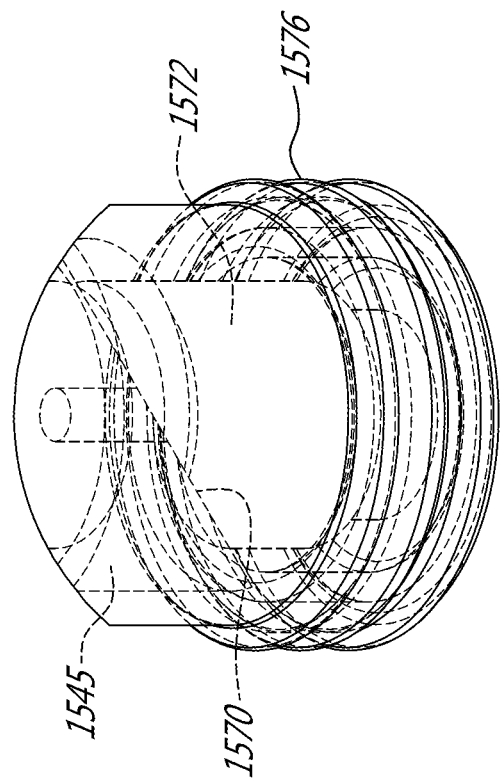
FIG. 29 is a fragmentary, perspective view showing the embodiment of FIG. 28.
Figure 28:
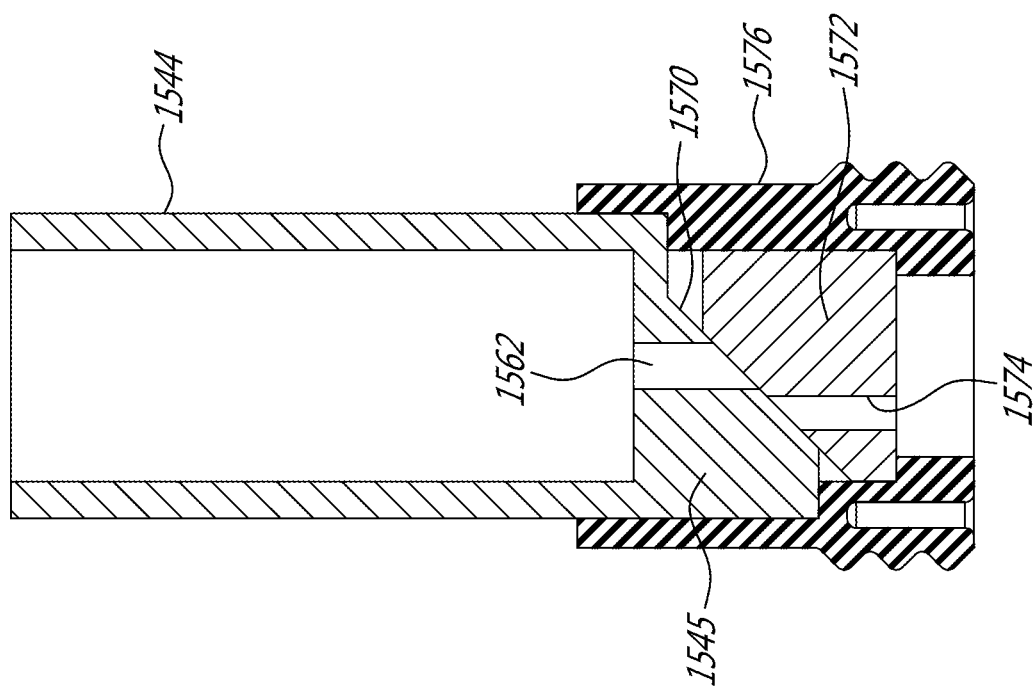
FIG. 28 is a longitudinal cross section taken though part of an injector showing yet another embodiment of the detail thereof.

A similar embodiment is shown in FIGS. 28 and 29 but the numerals have been raised by 100. In this embodiment the end wall 1545 has a sloped portion 1570 and an axial bore 1562. The elastomeric bladder 1576 retains the second block 1572, which has a bore 1574, in its default position such that the bores 1562 and 1574 are misaligned. However once axial pressure is provided to the barrel 1544, the bladder 1576 will tend to collapse, allowing the block 1572 to move axially and laterally on the slope 1570 until the bores 1562 and 1574 are aligned. The needle (not shown) can then pass through the aligned bores 1562 and 1574. Once pressure is released from the barrel 1544, the bladder 1576 will cause block 1572 two move against the slope 1570 towards its default position rendering the bores 1562 and 1574 out of alignment.

The invention claimed is:

1. A fluid delivery injector comprising:
    a syringe having:
        a barrel with a peripheral wall having a longitudinal axis and a distal end wall;
        a plunger movable with the barrel parallel to the longitudinal axis towards and away from the end wall;
        at least one hollow needle anchored at its proximal end to the plunger and extending parallel to the axis towards the end wall with the needle contained within the barrel;
        a fluid retention reservoir defined in at least the barrel; the fluid retention reservoir in fluid communication with inlet port of the needle when a volume confining pressure is applied to the fluid;
        an energy storage device is provided for retaining the plunger in a default position spaced from the end wall with the at least one hollow needle contained within the barrel and for returning the needle to the default position once the pressure is released from the plunger;
    whereby the needle is projected beyond the end wall of the barrel only when pressure is applied to the plunger in the direction of the distal end wall;
    wherein the plunger includes a closed cavity with an elastomeric membrane forming an expandable chamber in communication with the hollow needle and the fluid retention reservoir is formed within the barrel between the plunger and the end wall and is in communication with the expandable chamber through conduits defined in the plunger.

2. The fluid delivery injector as defined in claim 1, wherein the peripheral wall of the barrel is a collapsible energy storing material.

3. The fluid delivery injector as defined in claim 1, wherein the end wall is provided with a pierceable septum for sealingly engaging the needle.

4. The fluid delivery injector as defined in claim 1, wherein the syringe is provided with a press member of rigid material at the proximal end of the barrel associated with the plunger.

5. The fluid delivery injector as defined in claim 1, wherein fluid retention reservoir is defined in the barrel while the needle is provided with at least an inlet port at the proximal end of the needle communicating the hollow bore of the needle with the fluid in the reservoir.

6. The fluid delivery injector as defined in claim 2, wherein the peripheral wall of the barrel is an elastomeric material adapted to store energy whereby the volume confining pressure applied to the fluid is provided manually through the plunger and the elastomeric wall of the barrel.

7. The fluid delivery injector as defined in claim 6, wherein the end wall is a material suitable for a pierceable septum and the needle sealingly engages the end wall.

8. The fluid delivery injector as defined in claim 1, wherein the plunger is of rigid material and defines a recess surrounding part of the base of the needle where inlet ports are located.

9. The fluid delivery injector as defined in claim 8, wherein the plunger is made of an elastomer and defines a closed cavity, within the barrel, that forms the fluid retention reservoir and is in fluid communication with the hollow needle.

10. The fluid delivery injector as defined in claim 9, wherein the energy storing device includes a coil spring in the barrel between the end wall and the plunger for returning the plunger to its default position with the needle retracted into the barrel when pressure is released from the press member.

11. The fluid delivery injector as defined in claim 8, wherein a second fluid retention reservoir is formed within the barrel between the plunger and the end wall and at least a secondary needle extends through the end wall and is in communication with the second reservoir; an elastomeric bellows extends from the distal portion of the end wall defining a closed cavity and a second end wall in which the at least secondary needle is contained whereby separate liquid doses are retained within the first and second reservoirs respectively whereby when pressure is applied to the press member the needle and the at least secondary needle project beyond the end wall and the bellows to administer the separate liquids to the patient.

12. The fluid delivery injector as defined in claim 8, wherein the plunger is an elastomeric sleeve with a distal end wall and the press member is a rigid block inserted in the sleeve but spaced from the plunger distal end wall to form a cavity as an expansion chamber in communication with the hollow needle; the fluid retention reservoir is formed within the barrel between the end wall of the barrel and the plunger distal end wall; at least one bore extending through the plunger distal end wall in communication with the reservoir and the expansion chamber such that when pressure is applied to the press member the fluid will flow from the reservoir through the expansion chamber into the needle as the needle projects through the end wall of the barrel into the patient.

13. The fluid delivery injector as defined in claim 12, wherein the energy storage device is the elastomeric sleeve connected to and extending between the proximal end of the barrel and the plunger in order to retract the plunger and the needle when pressure is released from the plunger so that the needle is within the confines of the barrel.

14. The fluid delivery injector as defined in claim 8, wherein the plunger is an elastomeric sleeve with a distal end wall and the press member is a rigid block inserted in the sleeve but spaced from the plunger distal end wall to form a cavity as an expansion chamber in communication with the hollow needle; a conical bellows is provided within the barrel extending from the end wall concentrically with the axis of the needle such that the bellows defines the reservoir within the barrel and the plunger distal end wall and provides the volume confining pressure to the fluid in the reservoir.

15. The fluid delivery injector as defined in claim 8, wherein the plunger is integral with the press member and is a rigid cylinder movable in sliding contact with the barrel; an elastomeric bellows is concentric with the needle in sealing engagement with the end wall at the base thereof and the distal portion of the plunger at the apex thereof, defining the fluid retention reservoir; and the needle having an inlet port near the proximal end of the needle communicating the reservoir with the hollow needle whereby when pressure is applied to the press member the fluid will flow from the reservoir through the needle as the needle projects beyond the end wall of the barrel.

16. The fluid delivery injector as defined in claim 8, wherein the plunger is in the form of an elastomeric sleeve with a distal end wall and a second sleeve, having a pierceable distal end wall, provided for axial sliding movement within the elastomeric sleeve and defining a first cavity between the elastomeric sleeve and the second sleeve; a press member engaging the second sleeve for forming a sealed second cavity therewith; the needle being anchored in the elastomeric sleeve distal end wall at the proximal end of the needle and a portion of the proximal end of the needle protruding into the first cavity with the distal end of the needle projecting towards the end wall of the barrel; at least a secondary needle communicating with the barrel and anchored in the elastomeric distal end wall but extending into the first cavity; a first fluid retention reservoir formed in the barrel between the barrel end wall and the elastomeric distal end wall in communication with the secondary needle; a mixing chamber formed in the second cavity adapted to contain a separate component; the at least secondary needle in communication with the first reservoir whereby when pressure is applied to the press member, the second sleeve will move axially within the elastomeric sleeve and the needle as well as the secondary needle will pierce the pierceable end wall of the second sleeve and as the plunger continues its axial movement the fluid from the first reservoir enters the mixing chamber to form a solution with the second component and the solution flows into the hollow needle while the hollow needle projects through the barrel end wall.

17. The fluid delivery injector as defined in claim 1, wherein the end wall includes a device for blocking the travel of the needle, once the needle has been retracted, including a transverse bore intersecting the axis of the needle, a shuttle adapted for sliding movement along the bore with a shuttle bore for the passage of the needle when the needle is in a position within the barrel prior to delivering a liquid, and a spring in the bore urging the shuttle to a position with the shuttle bore misaligned with the needle when the needle has been retracted after delivery of the liquid.

18. The fluid delivery injector as defined in claim 1, wherein the end wall includes a device for blocking the travel of the needle, once the needle has been retracted, the device including:
 a rigid cap mounted for movement on the distal end of the barrel and including
  a cam track defined on one of the inner surface of the cap and the outer surface of the barrel and
  a cam follower on the other of the surfaces;
  an energy storage device within the cap and the barrel end wall;
  an opening defined in the cap axially aligned with the needle when the injector is in the default position,
 whereby the energy storage device is compressed when pressure is applied to project the needle from the opening in the cap, and when the pressure is removed, the energy storage device distends causing an interaction of the cam follower and the cam track to misalign the opening in the cap with the needle when the needle has been retracted.

19. The fluid delivery injector as defined in claim 16, wherein the hollow needle has an inlet port adjacent the proximal end thereof and the fluid communication between the reservoir and the hollow needle is through the inlet port.

\* \* \* \* \*